(12) United States Patent
Nagase

(10) Patent No.: US 11,816,580 B2
(45) Date of Patent: Nov. 14, 2023

(54) OPTIMAL SOLUTION DETERMINATION METHOD, OPTIMAL SOLUTION DETERMINATION PROGRAM, AND OPTIMAL SOLUTION DETERMINATION DEVICE

(71) Applicant: FUJIFILM Corporation, Tokyo (JP)

(72) Inventor: Masaya Nagase, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 915 days.

(21) Appl. No.: 16/513,202

(22) Filed: Jul. 16, 2019

(65) Prior Publication Data
US 2019/0340513 A1    Nov. 7, 2019

Related U.S. Application Data

(63) Continuation of application No. PCT/JP2018/006501, filed on Feb. 22, 2018.

(30) Foreign Application Priority Data

Mar. 15, 2017  (JP) ................. 2017-050214

(51) Int. Cl.
*G06N 3/126* (2023.01)
*G16B 30/00* (2019.01)
(Continued)

(52) U.S. Cl.
CPC ............. *G06N 3/126* (2013.01); *G06F 17/11* (2013.01); *G06N 5/01* (2023.01); *G16B 30/00* (2019.02)

(58) Field of Classification Search
CPC ........ G06N 3/126; G06N 5/003; G16B 30/00; G06F 17/11
(Continued)

(56) References Cited

U.S. PATENT DOCUMENTS

2003/0210210 A1* 11/2003 Ide .................. G02B 6/0043
345/30

FOREIGN PATENT DOCUMENTS

| JP | 2000-57124 A | 2/2000 |
|---|---|---|
| WO | WO 03/027262 A2 | 4/2003 |
| WO | WO 2004/047020 A1 | 6/2004 |

OTHER PUBLICATIONS

Lopes et al., "A feature selection technique for inference of graphs from their known topological properties, Revealing scale-free gene regulatory networks", Information Science 272 (2014) 1-15 (Year: 2014).*

(Continued)

*Primary Examiner* — Tsu-Chang Lee
(74) *Attorney, Agent, or Firm* — Birch, Stewart, Kolasch & Birch, LLP

(57) ABSTRACT

Provided is an optimal solution determination method for determining optimality of a solution in a combinatorial optimization problem using a computer, including uniformly extracting a plurality of solutions in a solution space of the combinatorial optimization problem as a plurality of first solutions, and estimating a maximum evaluation value in a case where solutions of a number that exceeds the number of the plurality of first solutions are assumed, on the basis of a plurality of first evaluation values respectively corresponding to the plurality of first solutions that are uniformly extracted, as a first maximum evaluation value Z. Further, in a case where a solution candidate (graph G_1) that belongs to a solution space is input (step S18), an evaluation value S_1 corresponding to the graph G_1 is acquired, the acquired evaluation value S_1 is compared with the first maximum evaluation value Z, and it is determined whether the evaluation value S_1 of the input graph G_1 is within a (Continued)

confidence interval of the first maximum evaluation value Z (whether the graph G_1 is a first optimal value or not).

13 Claims, 20 Drawing Sheets

(51) Int. Cl.
  *G06F 17/11* (2006.01)
  *G06N 5/01* (2023.01)
(58) Field of Classification Search
  USPC .......................................................... 706/47
  See application file for complete search history.

(56) References Cited

OTHER PUBLICATIONS

Giddings et al., "Statistical Optimum Estimation Techniques for Combinatorial Optimization Problems: A Review and Critique," Journal of Heuristics, vol. 20. No. 3, 2014 (Published online Mar. 22, 2014), pp. 329-358.

Golden et al., "Interval Estimation of a Global Optimum for Large Combinatorial Problems," Naval Research Logistics Quarterly, vol. 26, 1979, pp. 69-77.

International Preliminary Report on Patentability and Written Opinion of the International Searching Authority, dated Sep. 26, 2019, for International Application No. PCT/JP2018/006501, with a Written Opinion translation.

International Search Report, dated May 22, 2018, for International Application No. PCT/JP2018/006501, with an English translation.

Iwashita et al., "ZDD-Based Computation of the Number of Paths in a Graph," TCS Technical Report, TSC-TRA-12-60, Hokkaido University, Sep. 18, 2012, pp. 1-12 (13 pages total).

Nakagawa et al., "Performance Evaluation with Extreme Statistics on Approximate Solution of Traveling Salesman Problem," Abstracts of the 2016 Fall National Conference of The Operations Research Society of Japan, Sep. 15, 2016, pp. 174-175 (3 pages total).

Someya, "Recent Trends in Development of Stochastic Optimization Algorithms", ST-13-018 to 028, The Papers of Technical Meeting on Systems, IEE Japan, Jun. 27, 2013, pp. 51-55 (6 pages total).

Tagawa et al., "Empirical Distribution and Solution by Difference Evolution of Optimization Problem Including Individual Opportunity Constraints," Information Processing Society of Japan, SIG Technical Reports, MPS, vol. 2017-MPS-112, No. 14, Feb. 20, 2017, pp. 1-6 (8 pages total).

Extended European Search Report for European Application No. 18768409.7, dated Mar. 19, 2020.

Wang et al., "Hybrid Binary Imperialist Competition Algorithm and Tabu Search Approach for Feature Selection Using Gene Expression Data," BioMed Research International, vol. 2016, Jun. 22, 2016, XP55675841A, pp. 1-12 (13 pages total).

European Office Action for European Application No. 18768409.7, dated Sep. 29, 2021.

Chinese Office Action for Chinese Application No. 201880009956.4, dated Sep. 5, 2022, with an English translation.

Chinese Office Action dated Apr. 17, 2023 for Application No. 201880009956.4 with an English translation.

Chinese Office Action for Chinese Application No. 201880009956.4, dated Aug. 8, 2023, with an English translation.

* cited by examiner

| GENE | X1 | X2 | ..... | Xn |
|------|-----|-----|-------|-----|
| A | 1.7 | 1.5 | ..... | 1.5 |
| B | 2.1 | 1.3 | ..... | 3.6 |
| ⋮ | ⋮ | ⋮ | ..... | ⋮ |
| Z | 1.1 | 0.1 | ..... | 2.4 |

FIG. 6

| $G_{(1)}$ | A | B | C | D |
|---|---|---|---|---|
| Ⓐ | 1 | 0 | 0 | 0 |

| $G_{(2)}$ | A | B | C | D |
|---|---|---|---|---|
| Ⓐ Ⓒ | 1 | 0 | 1 | 0 |

| $G_{(3)}$ | A | B | C | D |
|---|---|---|---|---|
| Ⓒ | 0 | 0 | 1 | 0 |

| $G_{(4)}$ | A | B | C | D |
|---|---|---|---|---|
| Ⓑ Ⓓ | 0 | 1 | 0 | 1 |

| (G) | A | B | C | D | Σ |
|---|---|---|---|---|---|
| (1) | 1 | 0 | 0 | 0 | 1 |
| (2) | 1 | 0 | 1 | 0 | 0 |
| (3) | 0 | 0 | 1 | 0 | 1 |
| (4) | 0 | 1 | 0 | 1 | 1 |
| Σ | 1 | 1 | 1 | 1 | 1 |

DETERMINATION LINE

{G₃, G₄}
Ⓑ Ⓒ Ⓓ

| (G) | A | B | C | D | Σ |
|---|---|---|---|---|---|
| (1) | 1 | 0 | 0 | 0 | 0 |
| (2) | 1 | 0 | 1 | 0 | 0 |
| (3) | 0 | 0 | 1 | 0 | 1 |
| (4) | 0 | 1 | 0 | 1 | 1 |
| Σ | 0 | 1 | 1 | 1 | 0 |

NG(0)

NG(0)

{G₂, G₃, G₄}
Ⓐ Ⓑ Ⓒ Ⓓ
      Ⓒ

| (G) | A | B | C | D | Σ |
|---|---|---|---|---|---|
| (1) | 1 | 0 | 0 | 0 | 0 |
| (2) | 1 | 0 | 1 | 0 | 1 |
| (3) | 0 | 0 | 1 | 0 | 1 |
| (4) | 0 | 1 | 0 | 1 | 1 |
| Σ | 1 | 1 | 2 | 1 | 0 |

OPTIMAL SOLUTION DETERMINATION METHOD, OPTIMAL SOLUTION DETERMINATION PROGRAM, AND OPTIMAL SOLUTION DETERMINATION DEVICE

CROSS-REFERENCE TO RELATED APPLICATIONS

The present application is a Continuation of PCT International Application No. PCT/JP2018/006501 filed on Feb. 22, 2018 claiming priority under 35 U.S.C § 119(a) to Japanese Patent Application No. 2017-050214 filed on Mar. 15, 2017. Each of the above applications is hereby expressly incorporated by reference, in their entirety, into the present application.

BACKGROUND OF THE INVENTION

1. Field of the Invention

The present invention relates to an optimal solution determination method, an optimal solution determination program, and an optimal solution determination device, and particularly to a technique for determining optimality of a solution in a combinatorial optimization problem.

2. Description of the Related Art

In recent years, needs for data analysis, such as data mining for big data, are growing. As one of important data analysis fields, there is a combinatorial optimization problem (for example, including a well-known traveling salesman problem, or the like).

The combinatorial optimization problem includes a lot of difficult problems such as a non-deterministic polynomial time (NP)-complete problem or an NP-hard problem. That is, generally, in a case where the scale of a problem gets bigger, a calculation amount explodes by an order of an exponential function or higher, and thus, solution based on exhaustive full search is almost not possible.

Accordingly, a variety of methods for heuristically calculating an approximate solution have been developed and applied. However, since full search is not performed, an obtained solution is merely limited to a "local solution". Accordingly, it is not possible to determine whether the obtained solution is a true optimal solution or not.

In order to directly handle such a problem, a research for finding out optimality of a solution by giving a certain score to a solution and performing statistical analysis together has been proposed. For example, a method for estimating a maximum score through extreme value statistical analysis has been proposed (Golden, B. L. and Alt, F. B. "Interval estimation of a global optimum for large combinatorial problems", Naval Research Logistics Quarterly, 26, 69-77 (1979)).

However, in a combinatorial optimization problem in which complicated constraint conditions are given depending on occasions, it is considered that it is difficult to provide means for uniformly extracting a large amount of solution candidates from a solution space that is a premise of good-quality statistical analysis, and thus, it is difficult to lead to practical application (Giddings, A. P., Rardin, R. L., and Uzsoy, R. "Statistical optimum estimation techniques for combinatorial optimization problems: a review and critique", Journal of Heuristics, 20(3), 329-358 (2014)).

Further, in relation to a combinatorial optimization problem, there is a data structure called a zero-suppressed binary decision diagram (ZDD). It is known that the ZDD can enumerate and index extremely large-scale combination sets with efficiency using a construction algorithm called a frontier method, which has been actively researched in recent years (Iwashita, H., Kawahara, J., and Minato, S. "ZDD-Based Computation of the Number of Paths in a Graph", TCS Technical Report, TCS-TR-A-12-60, Hokkaido University, Sep. 19, 2012.).

Further, in an innovative drug development field, large-scale gene data, for example, ribonucleic acid (RNA) expression matrix data can be acquired by a next generation sequencer (NGS) or the like that has been recently developed. Analysis of big data acquired in this way has attracted attention as bioinformatics. For example, there is an attempt for clarifying an action mechanism or the like based on a biological function. As an example, there is estimation of a gene control network. The gene control network refers to an analysis method for perceiving a system in which genes mutually controls expression levels as a stochastic graph model such as Bayesian network.

WO2004/047020A discloses a technique using a Bayesian model based on non-parametric regression for estimating a network relationship between genes from time-series researches of gene expression.

SUMMARY OF THE INVENTION

In such a gene control network, a graph in which genes are represented as nodes and a control relationship is represented as an edge is considered. Further, a graph search (graph mining) problem for calculating how much RNA expression matrix data obtained through a graph structure can be described and searching for a graph that is most suitable for the obtained data should be solved. However, with respect to the number of genes N, a possible number of graphs is $2^{(N^2)}$, and super-exponentially divergence occurs as N becomes large. In addition, in the Bayesian network model, a complicated restraint condition called a directed acyclic graph (DAG) restraint should be considered. In a case where the number of genes becomes large to some extent, it is difficult to describe the entirety of a solution space even in the ZDD.

However, an innovative drug development project is to produce a medicine which may be offered to a human body, which requires a long time and huge cost up to proof of a result, and, an industrial interest, particularly, an interest in validity of its analysis result is high. Accordingly, if optimality of a graph for clearly describing acquired RNA expression matrix data can be determined, it is extremely useful in industrial application.

A method for constructing a gene control network disclosed in WO2004/047040A is a method for acquiring change-with-time data of gene expression with respect to some genes, correcting a Bayesian estimation method, and determining a relationship between a cause and an effect of expressed genes. The correction of the Bayesian estimation method includes estimation of the cause and effect relationship between the expressed genes using the change-with-time data. The method disclosed in WO2004/047040A is a method for providing a network solution with high reliability by correcting the Bayesian estimation and non-parametric regression on the basis of an assumption that there is not much possibility that change of genes with late expression may be a cause of change of genes with fast expression, but there is no guarantee that such an assumption is applied to all types of gene control networks.

The present invention has been made in consideration of the above-mentioned problems, and an object of the invention is to provide an optimal solution determination method, an optimal solution determination program, and an optimal solution determination device capable of efficiently and accurately performing determination of optimality of a solution in a combinatorial optimization problem.

According to an aspect of the present invention, there is provided an optimal solution determination method for determining optimality of a solution in a combinatorial optimization problem using a computer, comprising: a first step of uniformly extracting a plurality of solutions in a solution space of the combinatorial optimization problem as a plurality of first solutions; a second step of acquiring a plurality of first evaluation values respectively corresponding to the plurality of first solutions that are uniformly extracted in the first step; a third step of estimating a maximum evaluation value in a case where solutions of a number that exceeds the number of the plurality of first solutions are assumed, on the basis of the acquired plurality of first evaluation values, and setting the estimated maximum evaluation value as a first maximum evaluation value; a fourth step of acquiring at least one solution among solutions that belong to the solution space as a solution candidate; a fifth step of acquiring an evaluation value corresponding to the solution candidate; a sixth step of determining whether the evaluation value corresponding to the solution candidate acquired in the fifth step is within a confidence interval of the first maximum evaluation value; and a seventh step of setting the solution candidate as a first optimal solution in a case where it is determined in the sixth step that the evaluation value corresponding to the solution candidate is within the confidence interval of the first maximum evaluation value.

According to the aspect of the present invention, the plurality of solutions in the solution space of the combinatorial optimization problem are uniformly extracted as the plurality of first solutions, the first maximum evaluation value in a case where the solutions of the number that exceeds the number of the plurality of first solutions that are uniformly extracted are assumed is estimated as the maximum evaluation value. Further, in a case where at least one solution among the solutions that belong to the solution space is acquired as the solution candidate, the evaluation value corresponding to the solution candidate is acquired, and it is determined whether the acquired evaluation value is within the confidence interval of the first maximum evaluation value (whether or not the solution candidate is one of the first optimal solutions). Thus, it is possible to achieve statistical optimality determination of solutions in a combinatorial optimization problem, and it is possible to perform determination of optimality relating to whether a solution satisfies a sufficient condition.

According to another aspect of the present invention, in the optimal solution determination method, it is preferable that the plurality of first solutions are U×V solutions when U and V are respectively natural numbers, and in the third step, the U×V solutions are divided into V blocks, V division maximum values of evaluation values of U solutions are acquired for the respective blocks, and the first maximum evaluation value is estimated using the V division maximum values assuming that the interval maximum values follow a generalized extreme value distribution. Further, the V division maximum values of the evaluation values of the U solutions for the respective blocks are acquired, and assuming that the interval maximum values follow a generalized extreme value distribution (GEV), the maximum evaluation value (the first maximum evaluation value) is obtained by maximum likelihood estimation using the V interval maximum values.

According to still another aspect of the present invention, in the optimal solution determination method, it is preferable that the method further comprises an eighth step of outputting a determination result in the seventh step.

According to still another aspect of the present invention, in the optimal solution determination method, it is preferable that a first search method in which computation cost is small and solution accuracy is low and a second search method in which computation cost is larger than that in the first search method and solution accuracy is higher than that in the first search method are provided. Further, it is preferable that in the fourth step, a first solution candidate that is first searched by the first search method is input, and only in a case where an evaluation value of the first solution candidate is not within a range of the first maximum evaluation value, a second solution candidate that is searched by the second search method is input.

The first solution candidate that is searched by the first search method in which the computation cost is small and the solution accuracy is low is first input. In a case where the first solution candidate does not satisfy a sufficient condition and the determination of the sufficiency is not successful, it is suggested that another optimal solution is present since the heuristic search by the first search method is not sufficient. In this case, the search is replaced with the search of the second solution candidate using the second search method in which the computation cost is large and the solution accuracy is high, and sufficiency of the second solution candidate searched by the second search method is determined.

According to still another aspect of the present invention, in the optimal solution determination method, it is preferable that the method further comprises a ninth step of uniformly extracting a plurality of solutions that are solutions in the solution space and are outside a range of a predetermined distance in the solution space from the first optimal solution, as a plurality of second solutions; a tenth step of acquiring a plurality of second evaluation values respectively corresponding to the plurality of second solutions; an eleventh step of estimating a maximum evaluation value in a case where solutions of a number that exceeds the number of the plurality of second solutions are assumed, on the basis of the plurality of second evaluation values, and setting the estimated maximum evaluation value as a second maximum evaluation value; a twelfth step of acquiring an evaluation value of the first optimal solution; and a thirteenth step of determining whether the evaluation value of the first optimal solution exceeds the second maximum evaluation value.

According to the aspect of the present invention, the plurality of solutions that are outside the range of the predetermined distance in the solution space from the first optimal solution are uniformly extracted as the plurality of second solutions, and the maximum evaluation value in a case where the solutions of the number that exceeds the number of the plurality of second solutions that are uniformly extracted are assumed is estimated as the second maximum evaluation value. Further, it is determined whether the evaluation value of the first optimal solution exceeds the second maximum evaluation value. Thus, it is possible to perform determination of optimality relating to whether a solution of a combinatorial optimization problem satisfies a necessary condition, and in a case where the evaluation of the first optimal solution exceeds the second maximum evaluation, the first optimal solution satisfies a necessary sufficient condition, and becomes an optimal solution in the solution space, which means that an equivalent solution is not present any more.

According to still another aspect of the present invention, in the optimal solution determination method, it is preferable that the plurality of second solutions are P×Q solutions when P and Q are respectively natural numbers, and in the eleventh step, the P×Q solutions are divided into Q blocks, Q interval maximum values of evaluation values of P solutions for the respective blocks are acquired, and the second maximum evaluation value is estimated using the Q interval maximum values assuming that the interval maximum values follow a generalized extreme value distribution. The Q interval maximum values of the evaluation values of the P solutions for the respective blocks are acquired, and assuming that the interval maximum values follow a generalized extreme value distribution, the maximum evaluation value (the second maximum evaluation value) is obtained by maximum likelihood estimation using the Q interval maximum values.

According to still another aspect of the present invention, in the optimal solution determination method, it is preferable that the method further comprises a fourteenth step of outputting a determination result in the thirteenth step.

According to still another aspect of the present invention, in the optimal solution determination method, it is preferable that the method further comprises a fifteenth step of enlarging the range of the predetermined distance in a case where it is determined in the thirteenth step that the evaluation value of the first optimal solution does not exceed the second maximum evaluation value, and uniformly extracting a plurality of solutions outside the enlarged range of the predetermined distance as a plurality of third solutions; a sixteenth step of acquiring a plurality of third evaluation values respectively corresponding to the plurality of third solutions; a seventeenth step of estimating a maximum evaluation value in a case where solutions of a number that exceeds the number of the plurality of third solutions are assumed, on the basis of the plurality of third evaluation values, and setting the estimated maximum evaluation value as a third maximum evaluation value; and an eighteenth step of determining whether the evaluation value of the first optimal solution exceeds the third maximum evaluation value.

In a case where the evaluation value of the first optimal solution searched as one optimal solution does not exceed the second maximum evaluation value, there is a possibility that the equivalent optimal solution is present, but in this case, the third maximum evaluation value is estimated again on the basis of the plurality of third solutions that are uniformly extracted from a solution space (a solution space outside the enlarged predetermined range) spaced from the first optimal solution. Thus, it is possible to confirm that the equivalent optimal solution is not present in the solution space spaced from the searched optimal solutions.

According to still another aspect of the present invention, in the optimal solution determination method, it is preferable that the method further comprises: a nineteenth step of acquiring a fourth solution candidate that is a solution in the solution space and is spaced from the first optimal solution by a predetermined distance in a case where it is determined in the thirteenth step that the evaluation value of the first optimal solution does not exceed the second maximum evaluation value; a twentieth step of uniformly extracting a plurality of fourth solutions that are outside a range of a predetermined distance in the solution space from each of the first optimal solution and the fourth solution candidate, in the solution space; a twenty first step of acquiring a plurality of fourth evaluation values respectively corresponding to the plurality of fourth solutions; a twenty second step of estimating a maximum evaluation value in a case where solutions of a number that exceeds the number of the plurality of fourth solutions are assumed, on the basis of the plurality of fourth evaluation values, and setting the estimated maximum evaluation value as a fourth maximum evaluation value; and a twenty third step of determining whether the evaluation value of the first optimal solution exceeds the fourth maximum evaluation value.

In a case where the evaluation value of the first optimal solution searched as one optimal solution does not exceed the second maximum evaluation value, the plurality of fourth solutions that are outside the range of the predetermined distance in the solution space are uniformly extracted from each of the first optimal solution and the fourth solution candidate that is spaced from the first optimal solution by a predetermined distance, and the fourth maximum evaluation value is estimated again on the basis of the plurality of fourth solutions that are uniformly extracted. Thus, it is possible to confirm that the equivalent optimal solution is not present in the solution space spaced from each of the searched first optimal solution and the fourth solution candidate in the solution space outside the predetermined range.

According to still another aspect of the present invention, in the optimal solution determination method, it is preferable that the solution space includes a first solution space in a first constraint condition and a second solution space in a second constraint condition and the method further comprises: a twenty fourth step of acquiring the first solution candidate that belongs to the first solution space; a twenty fifth step of uniformly extracting a plurality of solutions in the second solution space as a plurality of fifth solutions; a twenty sixth step of acquiring a plurality of fifth evaluation values respectively corresponding to the plurality of fifth solutions; a twenty seventh step of estimating a maximum evaluation value in a case where solutions of a number that exceeds the number of the plurality of fifth solutions are assumed, on the basis of the plurality of acquired fifth evaluation values, and setting the estimated maximum evaluation value as a fifth maximum evaluation value; a twenty eighth step of acquiring a solution that is a solution candidate in the second solution space and is at a close distance in the solution space from the first solution candidate acquired in the twenty fourth step as a neighborhood solution; a twenty ninth step of acquiring an evaluation value of the neighborhood solution; and a thirtieth step of determining whether the evaluation value of the neighborhood solution is within a confidence interval of the fifth maximum evaluation value.

According to the aspect of the present invention, in a case where the optimality of the solution candidate in the first solution space in the first constraint condition is determined, a neighborhood solution that is at a close distance in the solution space from the solution candidate and is in the second the second solution space in the second constraint condition is acquired, and optimality of the neighborhood solution is determined. That is, the determination of optimality of the neighborhood solution is substitutively used and the neighborhood solution is optimal, it is estimated that the solution candidate in the first solution space at a close distance to the neighborhood solution is also optimal.

According to still another aspect of the present invention, in the optimal solution determination method, it is preferable that the first step includes calculating a total number of solutions in the solution space using a data structure obtained by contracting combinable patterns, using at least one of a step of identifying whether to confirm non-suitability using a part of combinations without considering the remaining combinations, among the combinable patterns in the combinatorial optimization problem to reduce patterns to be identified or a step of extracting a common part of a pattern group with a difference in only a part of combinations among the combinable patterns and sharing the remaining combinations to reduce patterns to be identified, and by enumerating and indexing the contracted combinable patterns, generating a random number that is equal to or smaller than the calculated total number, and extracting solutions corresponding to patterns specified by the generated random number.

Thus, it is possible to uniformly extract solutions even in a combinatorial optimization problem of a tremendously large scale in which entire description is difficult even using an efficient unit, and thus, it is possible to perform solution optimality determination.

According to still another aspect of the present invention, in the optimal solution determination method, it is preferable that the combinatorial optimization problem is a combinatorial optimization problem of a gene control network.

According to still another aspect of the present invention, there is provided an optimal solution determination program causing a computer to execute the optimal solution determination method.

According to still another aspect of the invention, there is provided an optimal solution determination device that determines optimality of a solution in a combinatorial optimization problem, comprising: a solution extraction unit that uniformly extracts a plurality of solutions in a solution space of the combinatorial optimization problem as a plurality of first solutions; a first evaluation value acquisition unit that acquires a plurality of first evaluation values respectively corresponding to the plurality of first solutions that are uniformly extracted; a first maximum evaluation value estimation unit that estimates a maximum evaluation value in a case where solutions of a number that exceeds the number of the plurality of first solutions are assumed, on the basis of the plurality of acquired first evaluation values, and sets the estimated maximum evaluation value as a first maximum evaluation value; a solution acquisition unit that acquires at least one solution among solutions that belong to the solution space as a solution candidate; and a first determination unit that acquires an evaluation value corresponding to the solution candidate from the first evaluation value acquisition unit, determines whether the evaluation value corresponding to the acquired solution candidate is within a confidence interval of the first maximum evaluation value, and sets the solution candidate as a first optimal solution in a case where it is determined that the evaluation value corresponding to the solution candidate is within the confidence interval of the first maximum evaluation value.

According to still another aspect of the present invention, in the optimal solution determination device, it is preferable that the optimal solution determination device further comprises: a second solution extraction unit that uniformly extracts a plurality of solutions that are solutions in the solution space and are outside a range of a predetermined distance in the solution space from the first optimal solution, as a plurality of second solutions; a second evaluation value acquisition unit that acquires a plurality of second evaluation values respectively corresponding to the plurality of second solutions; a second maximum evaluation value estimation unit that estimates a maximum evaluation value in a case where solutions of a number that exceeds the number of the plurality of second solutions are assumed, on the basis of the plurality of second evaluation values, and sets the estimated maximum evaluation value as a second maximum evaluation value; and a second determination unit that acquires an evaluation value corresponding to the first optimal solution from the second evaluation value acquisition unit, and determines whether the acquired evaluation value corresponding to the first optimal solution exceeds the second maximum evaluation value.

According to the present invention, it is possible to achieve statistical optimality determination of solutions in a combinatorial optimization problem, and it is possible to efficiently perform the determination of the optimality of the solutions in the combinatorial optimization problem with high accuracy.

BRIEF DESCRIPTION OF THE DRAWINGS

FIG. 6 is a diagram showing four subsets ($G_{(1)}$, $G_{(2)}$, $G_{(3)}$, $G_{(4)}$).

FIG. 8 is a diagram showing three examples of "patterns" corresponding to selections of subsets and determination results indicating whether respective "patterns" satisfy conditions.

DESCRIPTION OF THE PREFERRED EMBODIMENTS

Here, preferred embodiments of an optimal solution determination method, an optimal solution determination program, and an optimal solution determination process according to the present invention will be described with reference to the accompanying drawings.

<Outline of the Present Invention>

As a method for searching for a solution in a combinatorial optimization method, a gene control network capable of being applied to an innovative drug development field will be described as an example. The gene control network refers to a method for expressing a cooperative relationship between genes as a directed graph, and is expected to be used in applications for analyzing an action mechanism or the like of a medicine, for example.

First, basic preconditions will be described.

Figure 1:
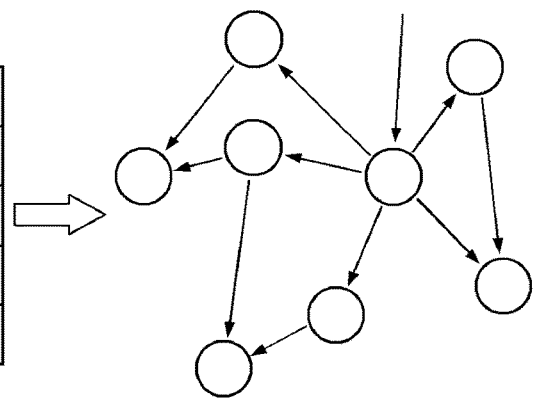
FIG. 1 is a diagram showing a graph showing RNA expression matrix data and a gene control network.

FIG. 1 shows a graph showing RNA expression matrix data and a gene control network.

In FIG. 1, A, B, . . . , and, Z represent genes, and X1, X2, . . . , and Xn represent samples, in which there is data corresponding to a product of the number of genes and the number of samples. RNA expression matrix data thereof is acquired. The RNA expression matrix data may be coverage data based on an NGS, or may be signal data based on microarray.

In the RNA expression matrix, an RNA expression level of N genes is measured with respect to M cell lines or the like, and data x(m, n) represents an expression level of a gene n in a cell line m. Accordingly, an RNA expression matrix D is M×N numerical value matrix data.

Relevancy of a plurality of genes may be expressed as a gene control network. Hereinafter, the gene control network is expressed as a graph G. As shown in FIG. 1, the graph G is a set of edges (control relationships between nodes (genes) indicated by arrows)). For example, g1={(A, B), (A, C), (C, D)} indicates that there are three control relationships of "gene A to gene B", "gene A to gene C", and "gene C to gene D". The graph G may be estimated from the RNA expression matrix data D in multiple samples.

Here, in the graph G, a certain constraint C is given according to problems. The constraint is given according to models or prior knowledge. For example, since a cyclic graph cannot be expressed in a Bayesian network model, the graph G should not be the cyclic graph (that is, for example, subsets such as "(A, B), (B, A)" or "(A, B), (B, C), (C, A)" should not be included). Further, in a case where a scale-free-network characteristic (that a degree distribution of nodes is suitable for a power law) is expected according to prior knowledge, such a constraint may be considered to be provided.

An evaluation function S(D, G) is prepared. This is obtained by quantifying how much the graph G can describe the data D. For example, in the above-described g1, with respect to the control relationship of "gene A to gene B", "whether x(m, B)=F(x(m, A)) is valid or not" is quantified. F is a model function of the control relationship, and in the quantification, for example, an Akaike's information criterion (AIC) or a Bayesian information criterion (BIC) is used.

A graph G_1 considered to be optimal is acquired through a certain heuristic method for solving an optimization problem, and an evaluation value S_1 therefor is acquired.

The above description shows an example of estimation of the gene control network, but main points are as follows: (a) on the basis of some data D, (b) a set G based on a constraint C is considered, (c) maximization (or minimization) of the evaluation function S is attempted, and (d) a specific set_1 is acquired. This is a general structure in a combinatorial optimization problem.

Accordingly, the present invention may also be applied to various other combinatorial optimization problems. For example, there is a problem for searching for exclusively coated gene mutation. In this regard, for example, an application for estimating an important gene mutation or action mechanism in cancer is known.

(1) With respect to M cells, mutation data x in N types of single nucleotide polymorphism (SNP) is acquired. Data x(m, n) represents the presence or absence of an SNP mutation n in a cell m. Here, the SNP refers to, among deoxyribonucleic acids (DNA), a DNA at a position where mutation easily enters.

(2) A set of gene loci is expressed as a set G. The set G is a set of SNPs. For example, g1={1, 3, 4} represents that three SNPs of "SNP 1, 3, 4" attract attention. Elements of the set G belong to the N types of SNPs, which correspond to SNP combination patterns in the entirety of the set G. Here, as a constraint C, it is necessary to exclusively coat the M cell lines by the set G. That is, in a case where "set M1 of cells with mutation in SNP1", "set M3 of cells with mutation in SNP3", and "set M4 of cells with mutation in SNP4" are considered, M1, M3, and M4 should not share cells that are elements that overlap each other and are not separated from each other, and all cells should be included in the entirety of M1, M3, and M4.

(3) An evaluation function S(G) is prepared. This is obtained by quantifying some characteristics of the set G. For example, a method for estimating optimality or the like when the set G of SNPs is loaded in a gene control network F that is already prepared is considered.

(4) A graph_1 that is considered to be optimal is acquired by a certain heuristic method, and an evaluation value_1 therefor is acquired.

As the above-described (4), for example, a greedy hill climbing method, a simulated annealing method, taboo search, genetic algorithms, or the like are known, and any one thereof may be used.

Further, the present invention may be applied to fields other than so-called bio informatics. For example, since estimation of a gene control network is generalized as a Bayesian network, the invention may be used as a method for measuring various characteristics of multiple products to be digitalized, and estimating a cause and effect relationship of the characteristics. As the combinatorial optimization problem, for example, a knapsack problem, a traveling salesman problem, or the like is known and applied to various fields. The present invention may be applied to any one of them.

In a normal heuristic search, since its algorithm is terminated in the above-described (4), it is not possible to determine whether the graph_1 acquired by the heuristic search is a true optimal value or not.

For example, in the case of a gene control network problem, it is not possible to determine whether the graph_1 is truly the most suitable for the RNA expression matrix data D or not. Accordingly, in order to step into an intervention test requiring a lot of money, it is necessary to perform a personalistic and uncertain process of scrutinizing the graph_1 by a biologist, for example, to determine validity.

Accordingly, the present invention has a configuration capable of identifying optimality of the graph_1 that is considered to be optimal.

Figure 2:
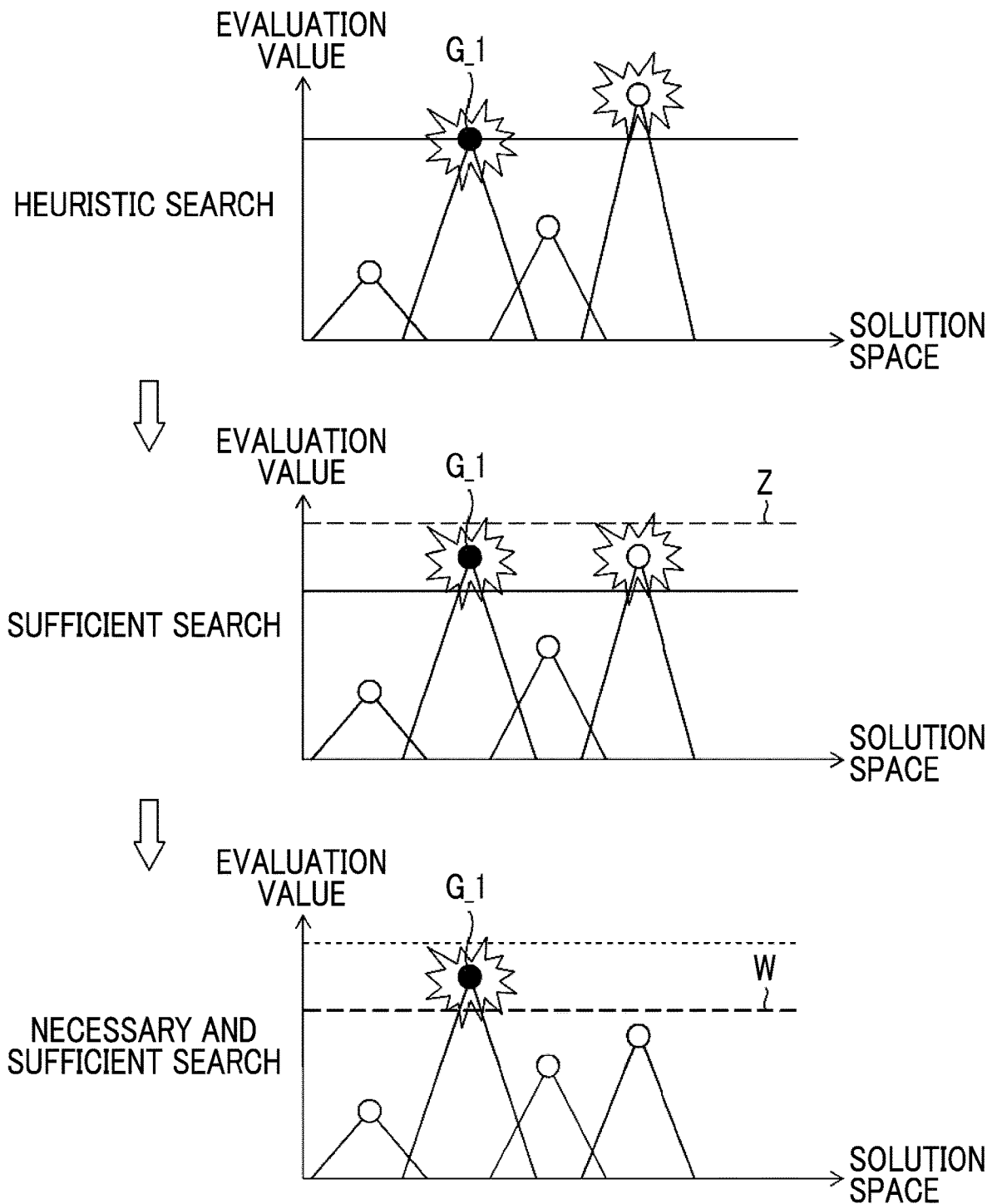
FIG. 2 is a conceptual diagram showing characteristics of the present invention.

FIG. 2 is a conceptual diagram showing characteristics of the present invention.

In order to identify optimality of the graph_1 that is considered to be optimal, searched through the heuristic search, a maximum evaluation value (a first maximum evaluation value) Z among evaluation values (evaluation values of solutions in an entire solution space (referred to as "scores")) in a case where solutions of a number that exceeds the number of extracted graphs searched through the heuristic search is assumed is estimated. A specific estimation method of the first maximum evaluation value Z will be described later.

Subsequently, it is determined whether the graph_1 (local solution) that is considered to be optimal is within a confidence interval of the estimated first maximum evaluation value Z. Further, in a case where the graph_1 is in the confidence interval of the first maximum estimation value Z, it can be determined that the graph_1 is a first optimal value (one of global solutions) in the entire area of the search space (solution space). Such a determination (sufficient optimality determination) of whether a solution satisfies a sufficient condition) is one of the characteristics of the present invention.

Here, in the case of the sufficient optimality determination, it is possible to determine whether a local solution is a global solution or not, but it is not possible to determine whether the local solution is a unique global solution or not. Accordingly, even in a case where the sufficient optimality determination of the graph_1 (local solution) is successful, there is a possibility that another equivalent solution may also be present, "regret" remains in the search.

In the present invention, in a case where the sufficient optimality determination of the graph_1 is successful, a maximum evaluation value (a second maximum evaluation value) W among evaluation values of solutions in a solution space (partial space) outside a range of a predetermined distance from the graph_1 in a solution space is estimated. A specific estimation method of the second maximum evaluation value W will be described later.

Subsequently, it is determined whether the graph_1 exceeds the estimated second maximum evaluation value W. Further, in a case where the graph_1 exceeds the second maximum evaluation value W, an equivalent solution as in the graph_1 is not present in the partial space, and thus, it is possible to determine that the graph_1 is a unique global solution. Such a determination (necessary optimality determination of whether a solution satisfies a necessary condition) is one of other characteristics of the present invention.

<Optimal Solution Determination Device>
[Device Configuration]

Figure 3:
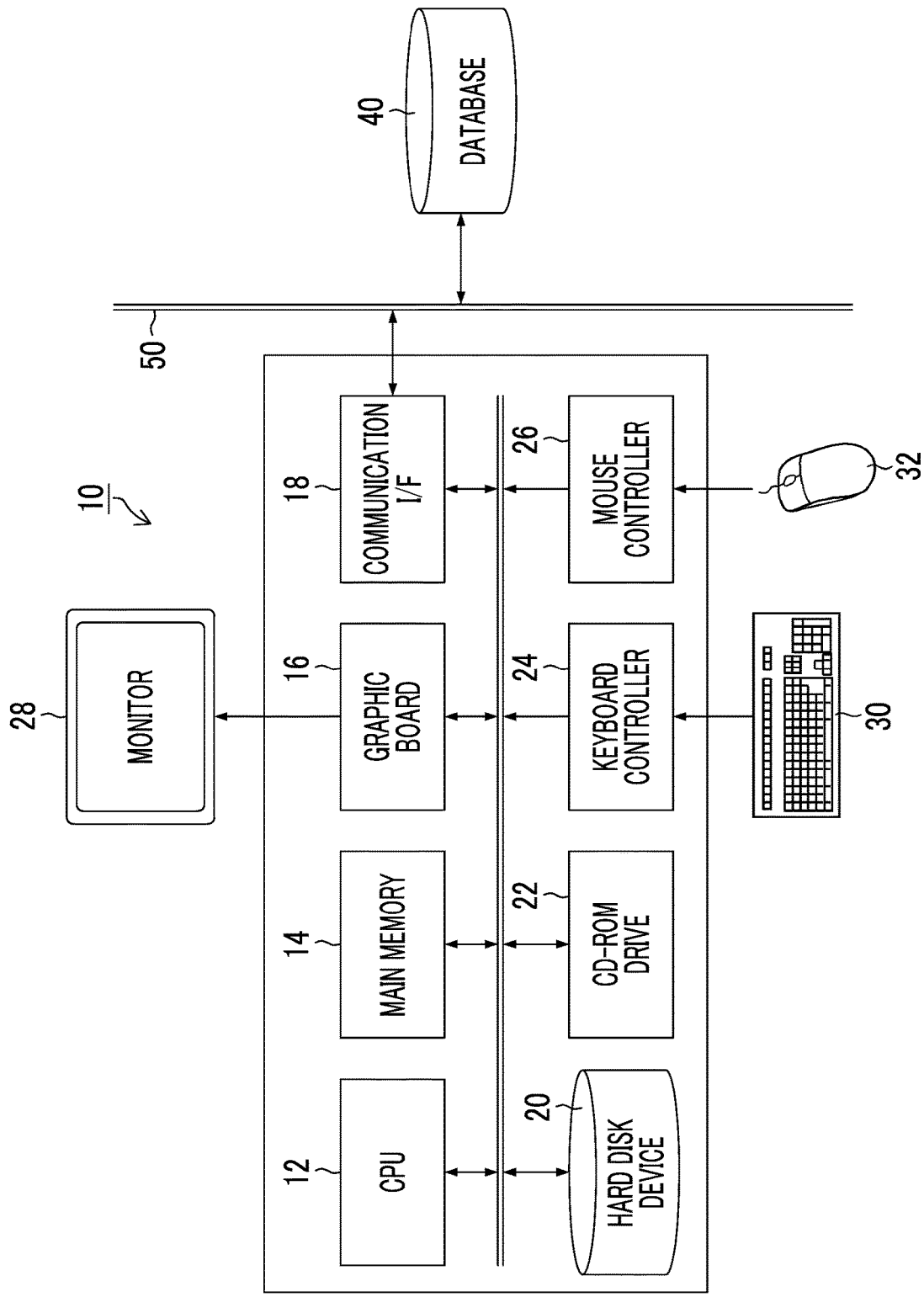
FIG. 3 is a block diagram showing a hardware configuration of an optimal solution determination device according to the present invention.

FIG. 3 is a block diagram showing a hardware configuration of an optimal solution determination device according to the present invention.

The optimal solution determination device 10 shown in FIG. 3 is configured of a computer, and includes, as main components, a central processing unit (CPU) 12 that controls operations of respective components, a main memory 14 that stores a device control program or serves as a work area in execution of the program, a graphic board 16 that controls display of a monitor device 28 such as a CRT display, a communication interface (communication I/F) 18 that is connected to a network 50, a hard disk device 20 that stores various applications including an optimal solution determination program according to the present invention and a determination result of an optimal solution to be described later, a CD-ROM drive 22, a keyboard controller 24 that detects a key operation of a keyboard 30 and outputs the result to the CPU 12 as a command input, a mouse controller 26 that detects a state of a mouse 32 that is a position input device and outputs a signal such as a position of a mouse pointer on the monitor device 28 or the state of the mouse 32 to the CPU 12.

Further, a database 40 that stores RNA expression matrix data is connected to the network 50. The RNA expression matrix data refers to numerical value matrix data indicating RNA expression levels of plural genes (A, B, ..., Z) in plural cell lines (samples: X1, X2, ..., Xn) as shown in FIG. 1. Further, the RNA expression levels are acquired from samples by a next generation sequencer (NGS) (not shown).

The optimal solution determination device 10 may access the database 40 through the communication interface 18 to acquire necessary RNA expression matrix data. The RNA expression matrix data is not limited to a case where RNA expression matrix data stored in the outside database 40 is used, and instead, RNA expression matrix data may be stored in the hard disk device 20 and the RNA expression matrix data stored in the hard disk device 20 may be used.

First Embodiment

Figure 4:
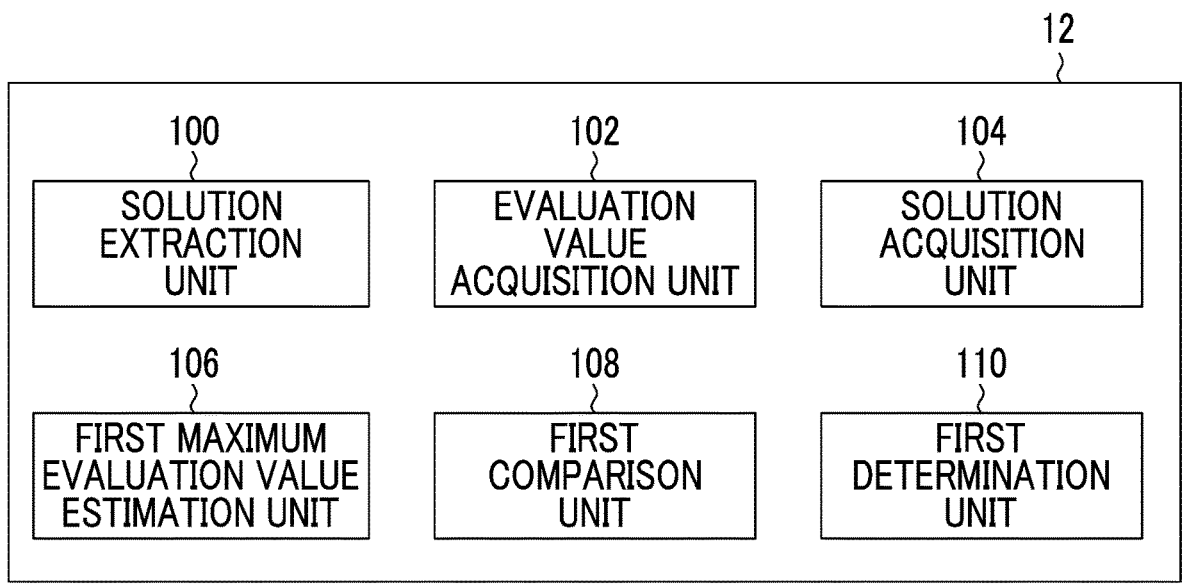
FIG. 4 is a functional block diagram showing a first embodiment of the present invention.

FIG. 4 is a functional block diagram showing a function of the CPU 12 of the optimal solution determination device 10 shown in FIG. 3, which is a functional block diagram showing a first embodiment of the present invention.

The CPU 12 functions as a variety of processing units by executing the optimal solution determination program stored in the hard disk device 20, and in the first embodiment shown in FIG. 4, functions as a solution extraction unit 100, an evaluation value acquisition unit 102 that functions as a first evaluation acquisition unit and a second evaluation value acquisition unit, a solution acquisition unit 104, a first maximum evaluation value estimation unit 106, a first comparison unit 108, and a first determination unit 110.

The solution extraction unit 100 is a portion that uniformly extracting solutions (graphs) in a solution space of a combinatorial optimization problem (gene control network), and enumerates and indexes the graphs G through a path enumerating and indexing algorithm using a zero-suppressed binary decision diagram (ZDD), in this example. By constructing the ZDD under the constraint C, it is possible to uniformly extract a total number of graphs G and unspecified elements of the set {G}. In the gene control network, a graph in which genes are nodes and control relationships are edges is considered.

Here, the "solution" means "feasible solution (executable solution)". An optimal solution is not particularly limited, but means a solution that is not an infeasible solution. That is, a non-suitable solution (that is infeasible) is excluded in advance.

Further, the solution extraction unit 100 contracts combinable patterns in a combinatorial optimization problem using at least one of "pruning" or "node sharing" to form a data structure to be enumerated and indexed. Here, the "pruning" refers to a process of identifying whether to confirm the non-suitability using a part of combinations without considering the remaining combinations, among the combinable patterns in the combinatorial optimization problem, to reduce patterns to be identified. Further, the "node sharing" of the frontier method refers to a process of extracting a common part of a pattern group with a difference in only a part of combinations among the combinable patterns and sharing the remaining combinations to reduce patterns to be identified.

This is not limited to only the ZDD, and a modified data structure similar to the ZDD such as a binary decision diagram (BDD) or a permutation decision diagram (TDD) may be used.

Further, in determination of the "non-suitability" based on the "pruning", the constraint C is used. For example, in the case of the gene control network, in a case where cycle is already generated by employed edges, the non-suitability is confirmed without considering the remaining edges. Further, in determination of "commonality" based on the "node sharing", in a similar manner, in consideration of a considered portion and remaining elements among patterns on the basis of the constraint C, the commonality is determined. For example, in a case where only the number of edges is considered, in a case where the number of employed edges is the same, the "node sharing" can be applied. Since the algorithm of "pruning" and "node sharing" is known as the frontier method in the case of the ZDD, the algorithm may be used.

As a technique that includes only the "pruning", a technique for enumerating solutions by a branch and bound method may be used. A method for negating the "node sharing" in the ZDD to enable enumeration based on the branch and bound method and negating the "pruning" may be considered. However, preferably, by using both the "pruning" and "node sharing" as in the ZDD, it is possible to efficiently enumerate solutions.

As a method for uniformly extracting solutions, for example, random generation may also be considered. That is, solution candidates are randomly generated (for example, the presence or absence of edges of a graph is determined by random numbers), re-generation is repeated in a case where constraint of G is not satisfied. In a case where a constraint condition is simple, the constraint may be incorporated in the step of random generation. For example, in a case where the number of edges is equal to or smaller than a predetermined number, an upper limit may be provided in a number for selecting the presence of edges. On the other hand, for example, in a case where a cyclic graph is to be prohibited, it is difficult to give a constraint in simple random generation, and thus, a method for determining whether the randomly generated graph is cyclic or not may be considered. However, theoretically, it is possible to perform statistical estimation by repeating the number of sufficient executions even in the random generation, but particularly, in a method for repeating determination and re-generation, in a case where a solution space under the constraint is small with respect to a solution space in which the random generation is covered, for example, in a case where the size of the solution space is set to be 1:N, it is necessary to perform N random generations on average to generate one solution, its efficiency is poor.

Accordingly, since it is important to secure a sufficient sample size in this method, it is expected that introduction of the ZDD is highly effective.

<Outline of ZDD>

Next, the ZDD and the frontier method will be described in detail.

First, application of the ZDD to a set partitioning problem that is a kind of combinatorial optimization problem is considered.

The set partitioning problem is a problem indicating whether, in a case where columns of subsets with respect to a certain whole set are given, patterns (combinations) such as "there is no duplication (mutually exclusive) in the selected subsets" and "the original whole set is completed (entirely coated)" are created through selection of some columns.

Figure 5:
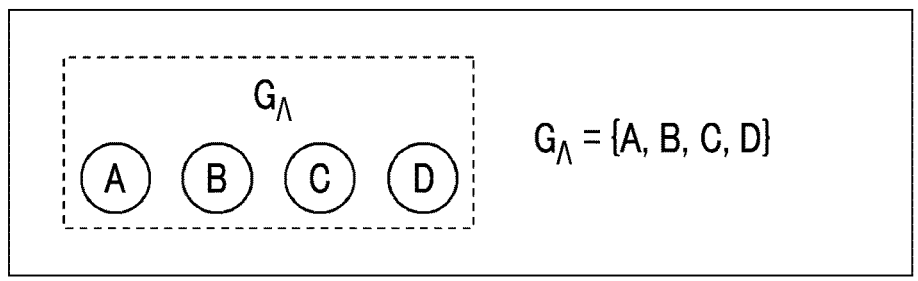
FIG. 5 is a diagram showing a whole set "GA" that includes elements "A, B, C, and D".

The set is defined as a "group of elements". As shown in FIG. 5, "GA" represents a whole set, and "A, B, C, and D" correspond to "elements".

In a case where the elements are fixed and the presence or absence of the elements are allocated "1 or 0", for example, subsets are determined as shown in FIG. 6.

Figure 7:
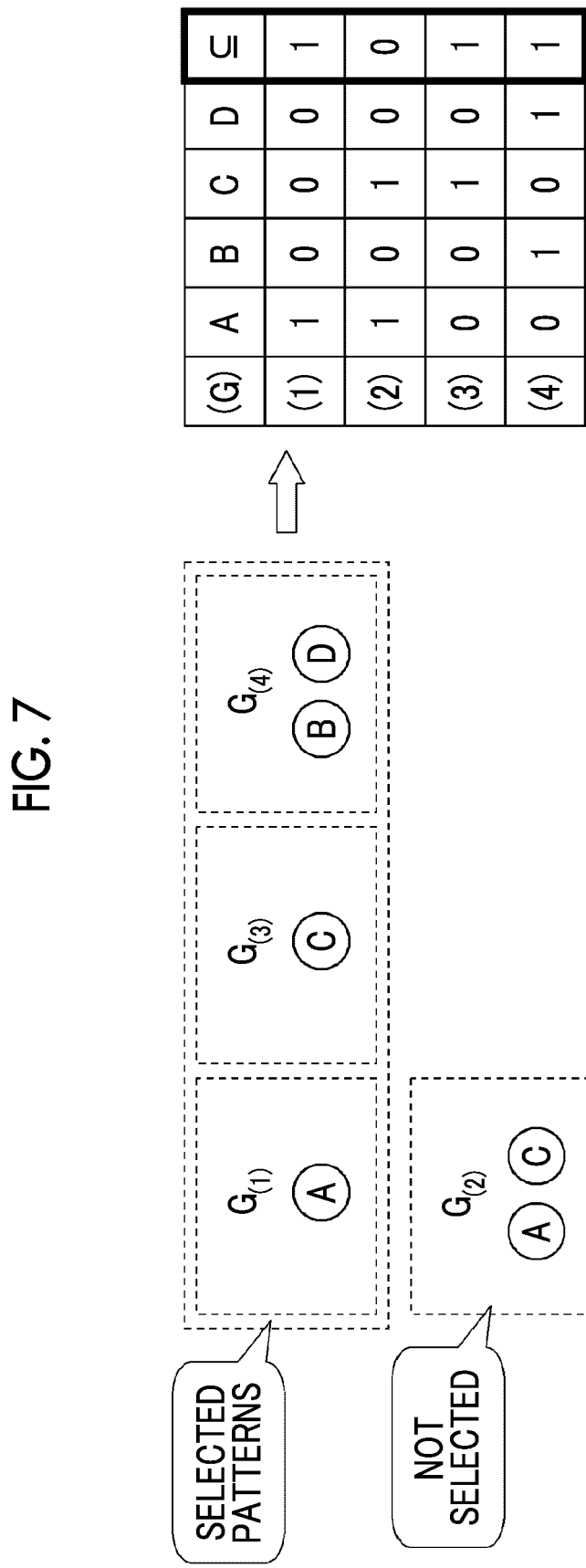
FIG. 7 is a diagram showing "patterns" corresponding to selections of three subsets ($G_{(1)}$, $G_{(3)}$, $G_{(4)}$).

In a case where "whether subsets are included" is coded, "patterns" may be expressed as shown in FIG. 7. In an example of FIG. 7, "patterns" corresponding to selection of three subsets ($G_{(1)}$, $G_{(3)}$, $G_{(4)}$) are shown.

Subsequently, it is determined whether "conditions (coating property and exclusiveness property) are satisfied" for each pattern.

FIG. 8 is a diagram showing three examples of "patterns" corresponding to selection of subsets and determination results indicating whether respective "patterns" satisfy the conditions.

As shown in FIG. 8, "patterns" corresponding to selection of the subsets ($G_{(1)}$, $G_{(3)}$, $G_{(4)}$) satisfy the conditions, and "patterns" corresponding to subsets ($G_{(2)}$, $G_{(3)}$, $G_{(4)}$) and subsets ($G_{(3)}$, $G_{(4)}$) do not satisfy the conditions.

The subsets ($G_{(2)}$, $G_{(3)}$, $G_{(4)}$) do not satisfy exclusiveness since element "C" overlaps, and the subsets ($G_{(3)}$, $G_{(4)}$) do not satisfy a coating characteristic since element "A" is not sufficient.

Figure 9:
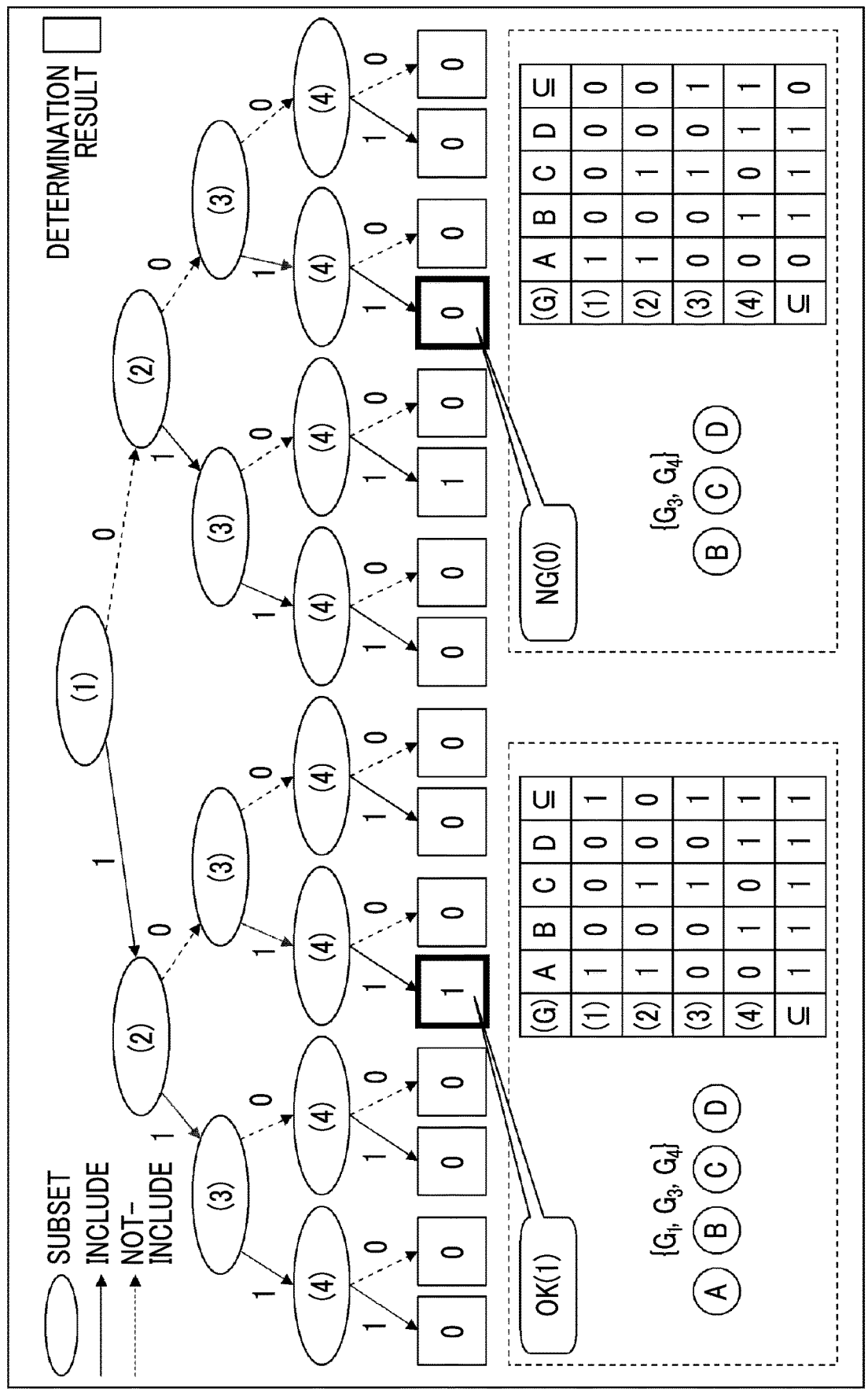
FIG. 9 is a diagram showing that all patterns and determination results in a set division problem shown in FIGS. 5 to 8 are comprehensively expressed as a "binary graph".

Thus, all patterns and determination results in the set partitioning problem in this example are comprehensively expressed in "binary graph" as shown in FIG. 9.

Since the number of subsets in this example is four, the number of all patterns is 16 ($=2^4$), but in a case where the number of subsets is N, the number of all patterns becomes $2^N$. In the expression of "binary graph", there is a problem in that branches are leaves increase in "$2^{\wedge}$".

In the combinatorial problem, it is known that "combinatorial explosion" occurs, and thus, an optimal solution cannot be searched in a limited time, but through a contraction technique of the "pruning" and "node sharing" of the frontier method, it is possible to realize efficient (practical) "enumeration" of combinatorial sets that satisfy a predetermined condition.

Figure 10:
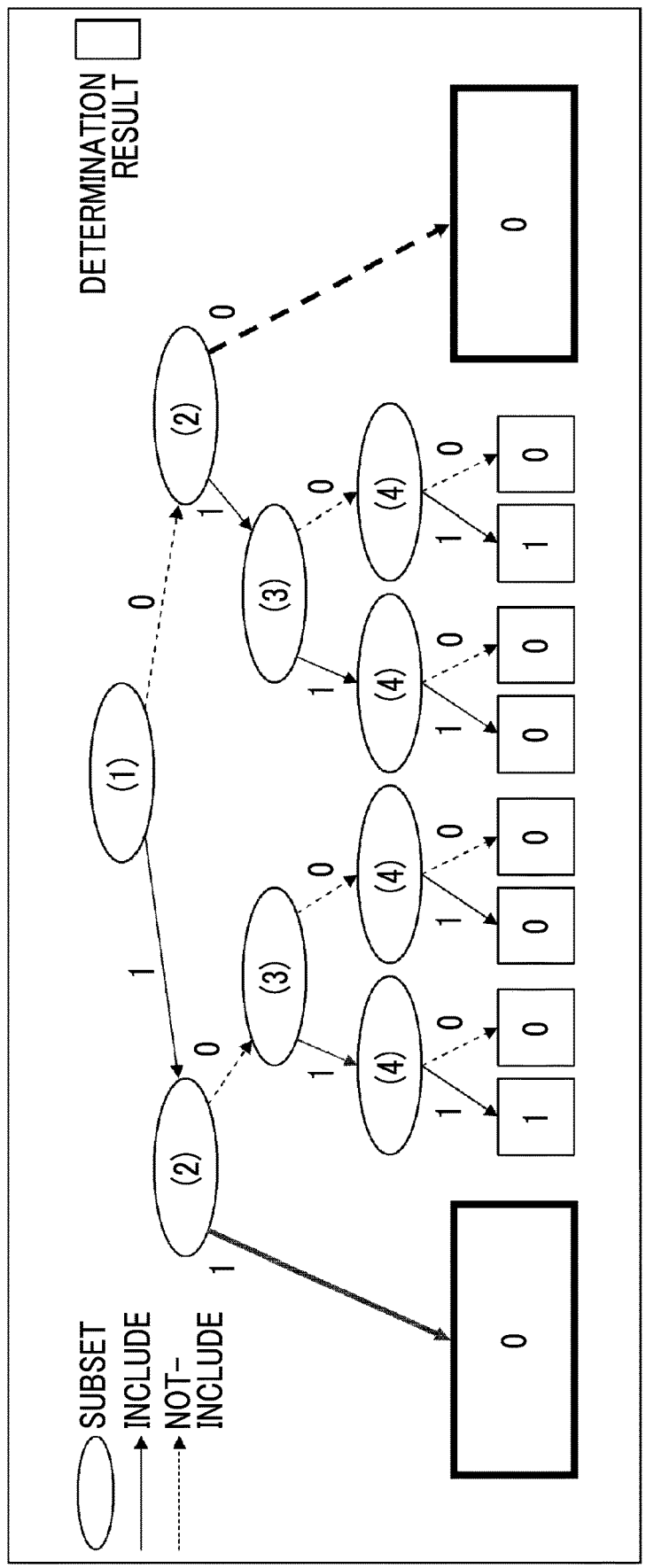
FIG. 10 is a diagram showing a state where combinable patterns are contracted by "pruning" of a frontier method.

FIG. 10 is a diagram showing a state where combinable patterns are contracted by the "pruning" of the frontier method.

As shown in FIG. 10, in a case where the subsets "$G_{(1)}$" and "$G_{(2)}$" are simultaneously selected, the element "A" is duplicated, and non-suitability is confirmed at the moment (regardless of subsequent selection). Similarly, in a case where both of the subsets "$G_{(1)}$" and "$G_{(2)}$" are not selected, the element "A" is missing, and thus, non-suitability is confirmed. Further, in a case where the non-suitability is confirmed, development is ended at the moment, which directly leads to "determination result=0".

As described above, in a case where non-suitability is confirmed in the middle of pattern selection, the "pruning" ends development at the moment to contract combinable patterns.

Figure 11:
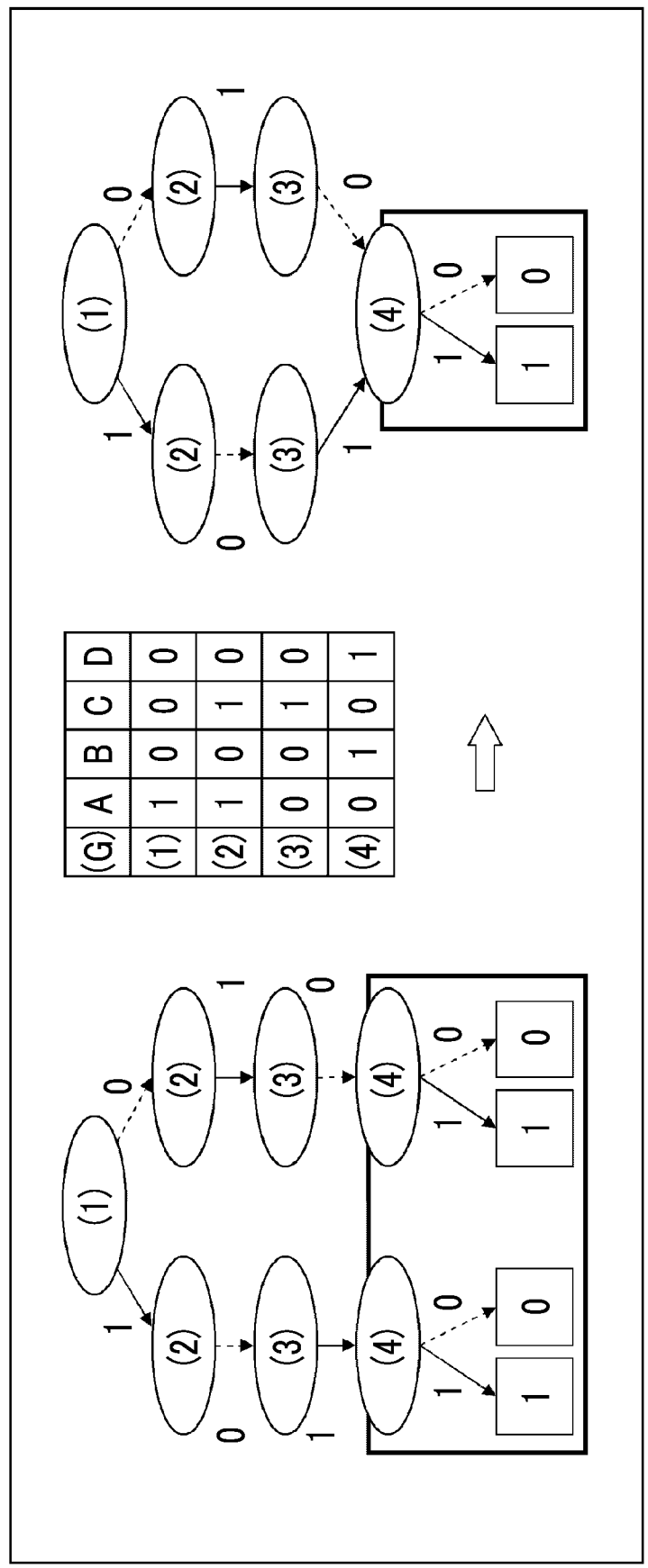
FIG. 11 is a diagram showing a state where combinable patterns are contracted by "node sharing" of the frontier method.

FIG. 11 is a diagram showing a state where combinable patterns are contracted by the "node sharing" of the frontier method.

As shown in FIG. 11, in a case where the two subsets "$G_{(1)}$" and "$G_{(3)}$" are selected, and in a case where one subset "$G_{(2)}$" is selected, since "elements "A" and "B" are to be included only once" and "elements "A" and "B" are not to be included any longer" become conditions in any case, acceptance determinations based on subsequent selections completely match.

Further, in this case, collective handling may be performed instead of separate development. That is, the same "node" may be shared.

In this way, the "node sharing" allows collective handing in a case where subsequent processes of a plurality of pattern selections are the same to contract combinable patterns.

Figure 12:
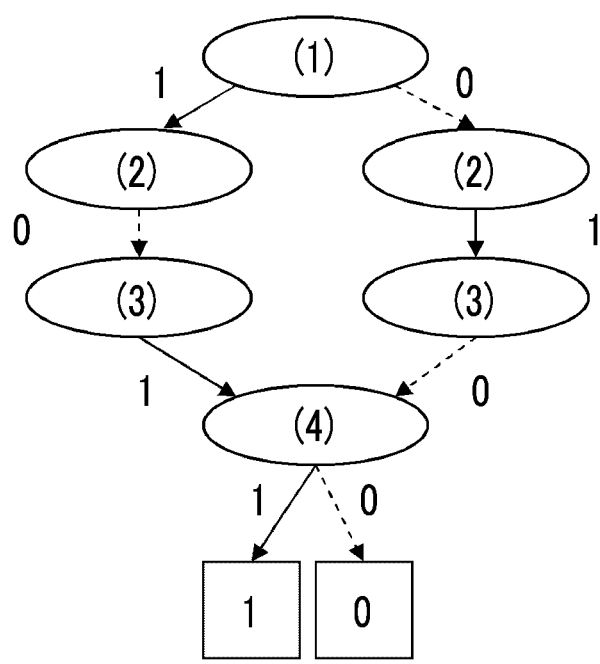
FIG. 12 is a diagram showing a result obtained by contracting combinable patterns by the "pruning" and "node sharing" of the frontier method.

FIG. 12 is a diagram showing a result obtained by contracting combinable patterns by the "pruning" and "node sharing" of the frontier method.

As shown in FIG. 12, it is possible to greatly reduce branches and leaves to be expanded to 16 patterns (FIG. 9), and to acquire a determination result that completely matches a case where determinations are comprehensively performed one by one.

Figure 13:
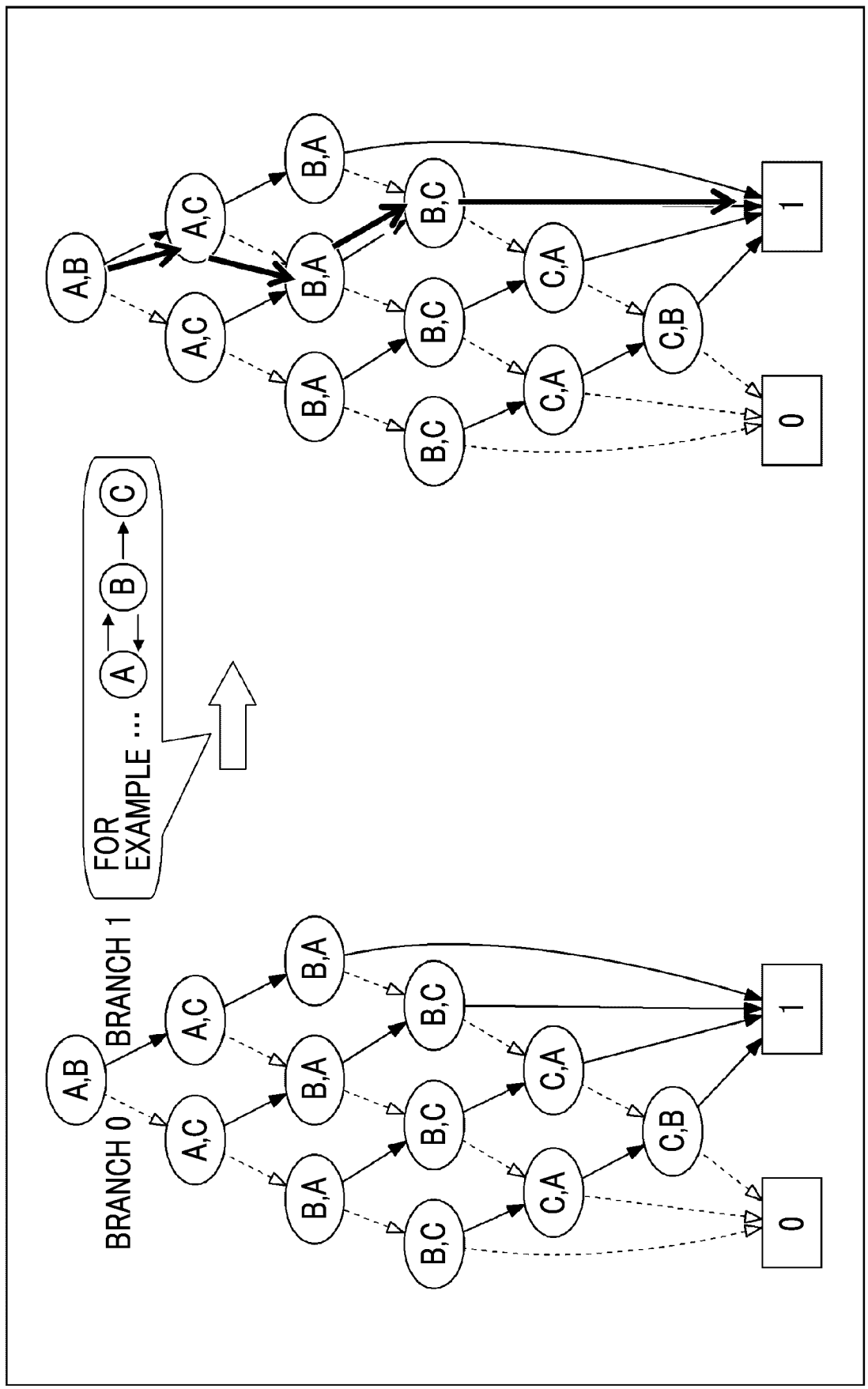
FIG. 13 is a diagram showing a figure indicating ZDD expression of a graph set in which the number of edges is 3 and a graph corresponding to a specific path (A⇔B⇒C), in nodes of {A, B, C}.

FIG. 13 is a diagram showing a ZDD expression of a graph set in which the number of edges is 3 in nodes of {A, B, C}.

In FIG. 13, graphs that include edges only when passing through "branch 1" indicated by solid lines (do not include "branch 0" indicated by dotted lines or skipped edges) and finally reach "end 1" are employed (graphs that reach "end 0" are not employed).

Here, for example, a graph corresponding to a path of (A⇔B⇒C) is expressed in a route indicated by a thick arrow on a right side in FIG. 13.

Figure 14:
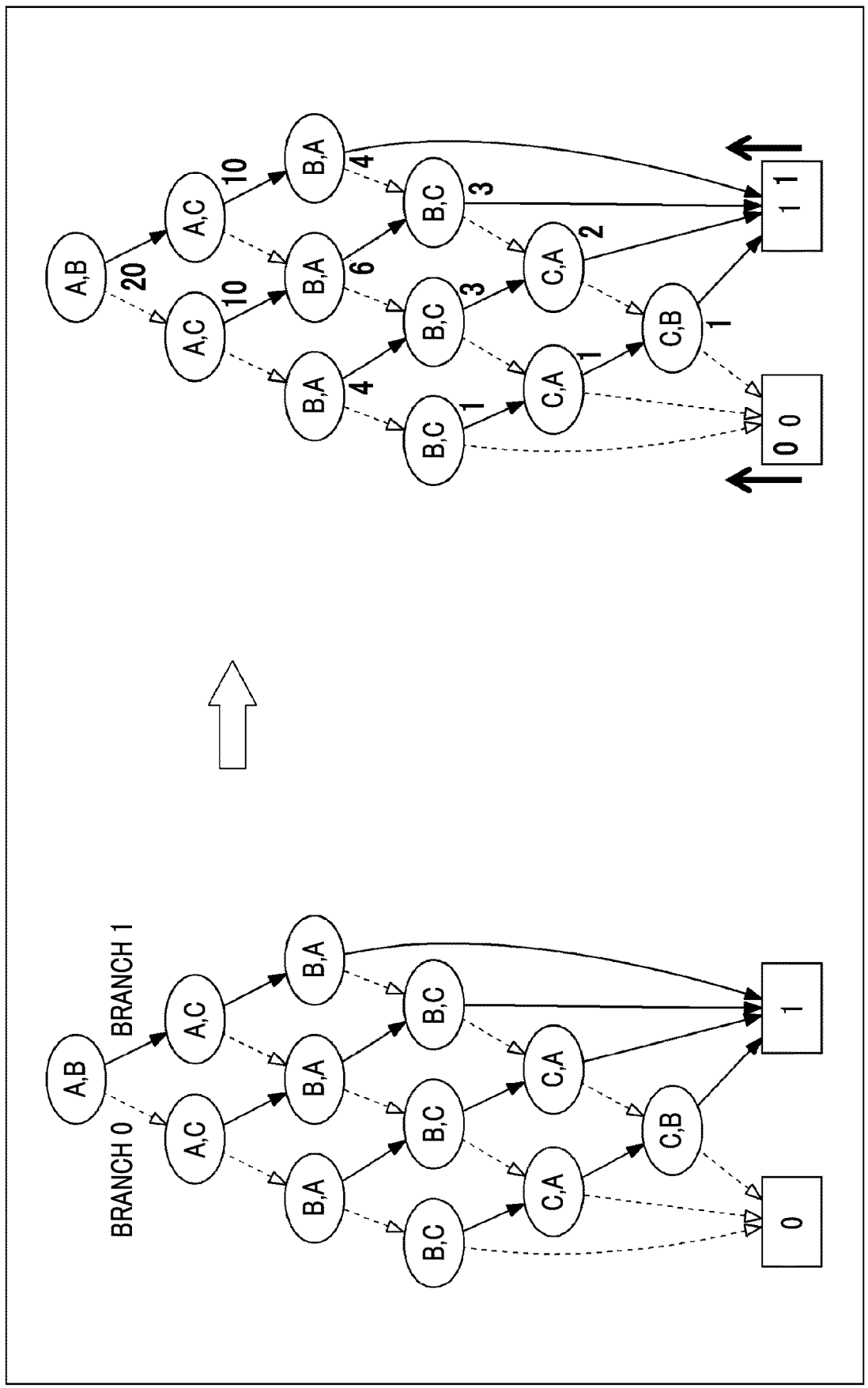
FIG. 14 is a diagram showing "enumeration" of a total number of graphs (total number of employments) of ZDD-expressed graph sets.

FIG. 14 is a diagram showing "enumeration" of a total number of graphs (a total number of employments).

As shown in FIG. 14, the total number of employments may be calculated by assigning "1" to "1 end" indicating the determination result and enumerating from the "1 end" to the highest ZDD node in a reverse order.

The enumeration is performed by adding up numbers assigned to respective branch destinations from a lower ZDD node, and assigning a number obtained by the addition to the branch destinations. This is repeated up to the highest ZDD node, and a numerical value assigned to the highest ZDD node becomes the total number of employments (a total number of paths that reach the "1 end"). In the case of this example, the total number of employments is 20.

The "enumeration" of calculating the total number of employments in this way is one of important characteristics of the ZDD.

Figure 15:
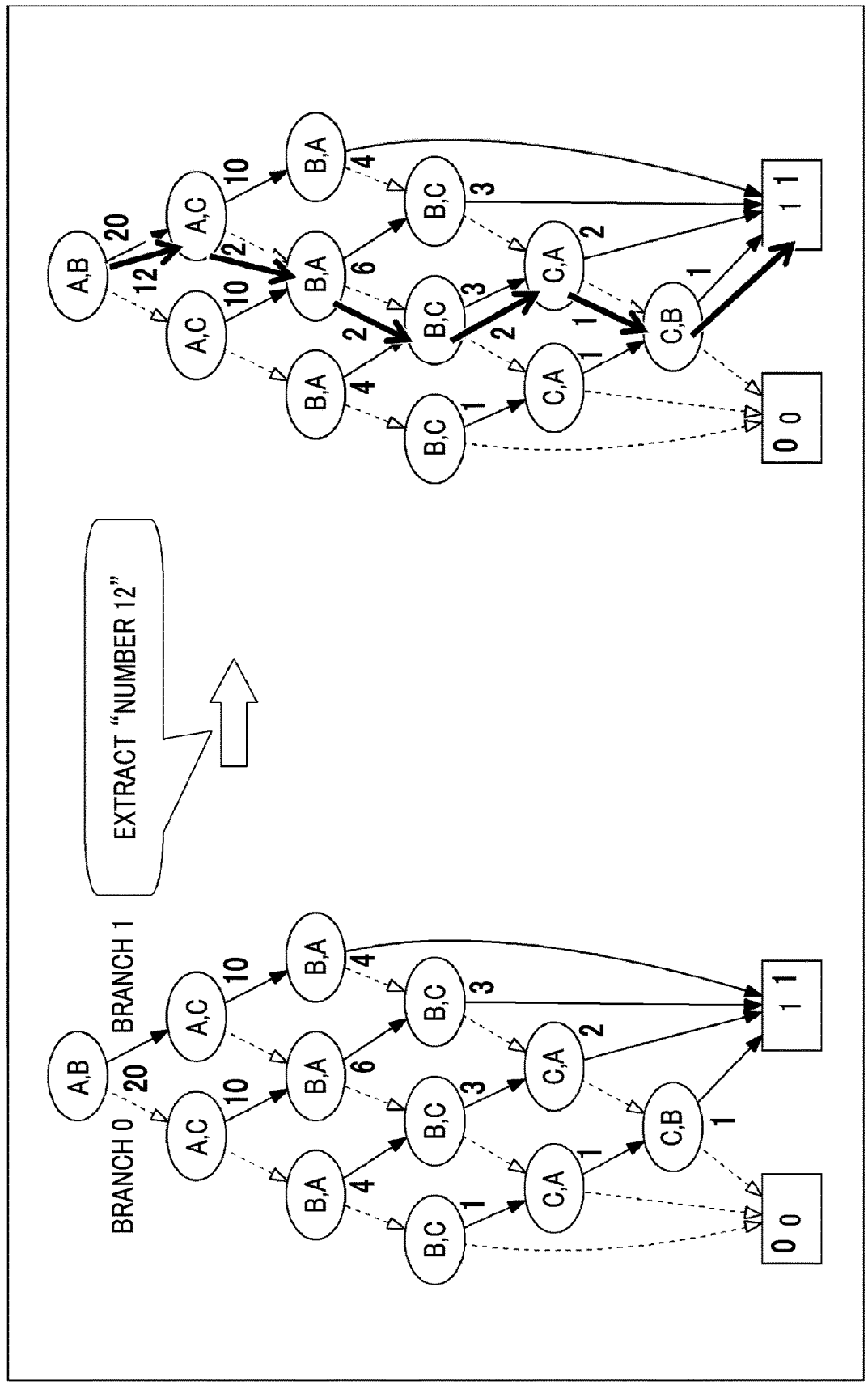
FIG. 15 is a diagram showing a method for extracting a graph of a certain designation number from the ZDD-expressed graph sets.

FIG. 15 is a diagram showing a method for extracting a graph of a certain designation number.

After the "enumeration", in a case where a certain number is designated (a number within the range of 1 to 20, in this case), by descending from the root in accordance with the designated number (designation number), it is possible to extract a graph corresponding to the designation number.

For example, in extracting a graph of "number 12", the process descends from the highest node along thick arrows in FIG. 15. First, the process proceeds from the highest node (A, B) to a branch including the designation number among "branch 0" or "branch 1". In this example, the process proceeds to a branch on the side of "branch 1", and descends from the highest node (A, B) to a lower node (A, C) (node (A, C) on a right side in FIG. 14). After the process proceeds to the branch on the side of "branch 1", a number on the side of "branch 0" is subtracted from the designation number. In this example, since the graph of "number 12" is to be extracted, a number "10" on the side of "branch 0" is subtracted from the designation number "12", which becomes "2". By repeating the subtraction until the process reaches "1 end", it is possible to extract a path (graph) indicated by the thick arrows in FIG. 15. Here, the graph of "number 12" shown in FIG. 15 is a graph corresponding to a path of (AB⇒B⇔C).

After the "enumeration" of the total number of employments is performed as described above, in a case where a certain number in the total number of employments is designated, it is possible to extract graphs that are uniformly specified by the designated number. Thus, by generating a random number that is equal to or smaller than the total number of employments, it is possible to "uniformly extract" solutions (graphs) in the solution space. The "uniform extraction" of the solutions in the solution space is one of the important characteristics of the ZDD.

Returning to FIG. 4, the solution extraction unit 100 uniformly extracts solutions (graphs G) in the solution space of the gene control network by the path column enumerating and indexing algorithm using the ZDD. A total number of graphs G in the solution space may be obtained by the "enumeration" that is one of the important characteristics of the ZDD. Further, by generating a random number (for example, a maximal length sequence (M sequence) that is equal to or smaller than the total number of the graphs G acquired by the "enumeration", it is possible to extract graphs G corresponding to the designated number designated by each random number (to uniformly extract the graphs G).

The evaluation value acquisition unit (first evaluation value acquisition unit) 102 assigns evaluation values to the graphs G extracted by the solution extraction unit 100. For example, an evaluation function S(D, G) obtained by quantifying how much the graphs G can describe the RNA expression matrix data D is prepared. Then, the evaluation value acquisition unit 102 acquires evaluation values S corresponding to the extracted graphs G on the basis of the evaluation function S(D, G), and assigns the acquired evaluation values S to the graphs G. The evaluation function S(D, G) may be created by the evaluation value acquisition unit 102 on the basis of the RNA expression matrix data stored in the database 40. Alternatively, the evaluation function S(D, G) created on the basis of the RNA expression matrix data in advance, and for example, stored in the database 40 may be used.

The solution acquisition unit 104 acquires a solution (solution candidate) (hereinafter, referred to as a "graph G_1") considered to be optimal, obtained by a certain heuristic method for solving an optimization problem of a gene control network. Further, an evaluation value S_1 for the input graph G_1 may be acquired by the evaluation value acquisition unit 102. As the heuristic method, for example, a greedy method, a hill climbing method, a simulated annealing method, taboo search, genetic algorithms, or the like are known, and any one thereof may be used. Further, the heuristic search may be performed by the present device, or may be performed by an external device. The solution acquisition unit 104 acquires solution candidate (graph G_1) obtained by any heuristic method.

The first maximum evaluation value estimation unit 106 is a unit that estimates a maximum evaluation value of solutions (graphs G) in a solution space. In this example, on the basis of evaluation values of a plurality of solutions (a plurality of first solutions) that are uniformly extracted by the solution extraction unit 100, the first maximum evaluation value estimation unit 106 estimates a maximum evaluation value (a first maximum evaluation value Z) among evaluation values in a case where solutions of a number that exceeds the number of the plurality of extracted first solutions is assumed.

Specifically, when U and V are natural numbers, respectively, U×V solutions (a plurality of first graphs G) are uniformly extracted, and evaluation values S are given to the respective graphs G. Here, U represents a block size, and V represents the number of blocks. The U and V are set to certain large values. For example, both of the U and V may be set to 10,000. In this case, the number of graphs G that are uniformly extracted becomes 100,000,000 (=10,000×10,000).

The first maximum evaluation value estimation unit 106 divides U×V graphs G into V groups, and acquires an interval maximum value among evaluation values of U groups G for each block. Accordingly, V interval maximum values may be acquired. Further, assuming that the V interval maximum values follow a generalized extreme value distribution (GEV), the maximum evaluation value (the first maximum evaluation value Z) is obtained by maximum likelihood estimation.

The first maximum evaluation value is accompanied by statistical support. The graphs {G} in the solution space are originally a limited set, and strictly speaking, are degenerated. However, since the number of groups G is sufficiently large, continuous distribution approximation may be applied thereto. In this case, since an upper limit is clearly present in the evaluation values S, it is expected that a Gumbel type distribution is achieved using appropriate setting of U and V, and thus, it is possible to estimate a true first maximum evaluation value Z with a confidence interval.

The first comparison unit 108 acquires the evaluation value S_1 corresponding to the solution candidate (graph G_1) acquired by the solution acquisition unit 104 from the evaluation value acquisition unit 102, and compares the acquired evaluation value S_1 with the estimated first maximum evaluation value Z with the confidence interval.

The first determination unit 110 determines whether the evaluation value S_1 of the graph G_1 is in the confidence interval of the first maximum evaluation value Z on the basis of the comparison result of the first comparison unit 108. In a case where the evaluation value S_1 of the graph G_1 is within the confidence interval of the first maximum evaluation value Z, it can be understood that the graph G_1 is one of the first optimal solutions ("graph G_1 is sufficient") in an entire area of the solution space.

In a case where Z»S_1, a difference between the two evaluation values is converted into a distance in the solution space, and it may be estimated how far the currently estimating graph G_1 is spaced from a true optimal solution (solution corresponding to the first maximum evaluation value Z).

That is, it may be determined whether the solution candidate (graph G_1) searched through the heuristic search is the true optimal value or not.

Second Embodiment

Figure 16:
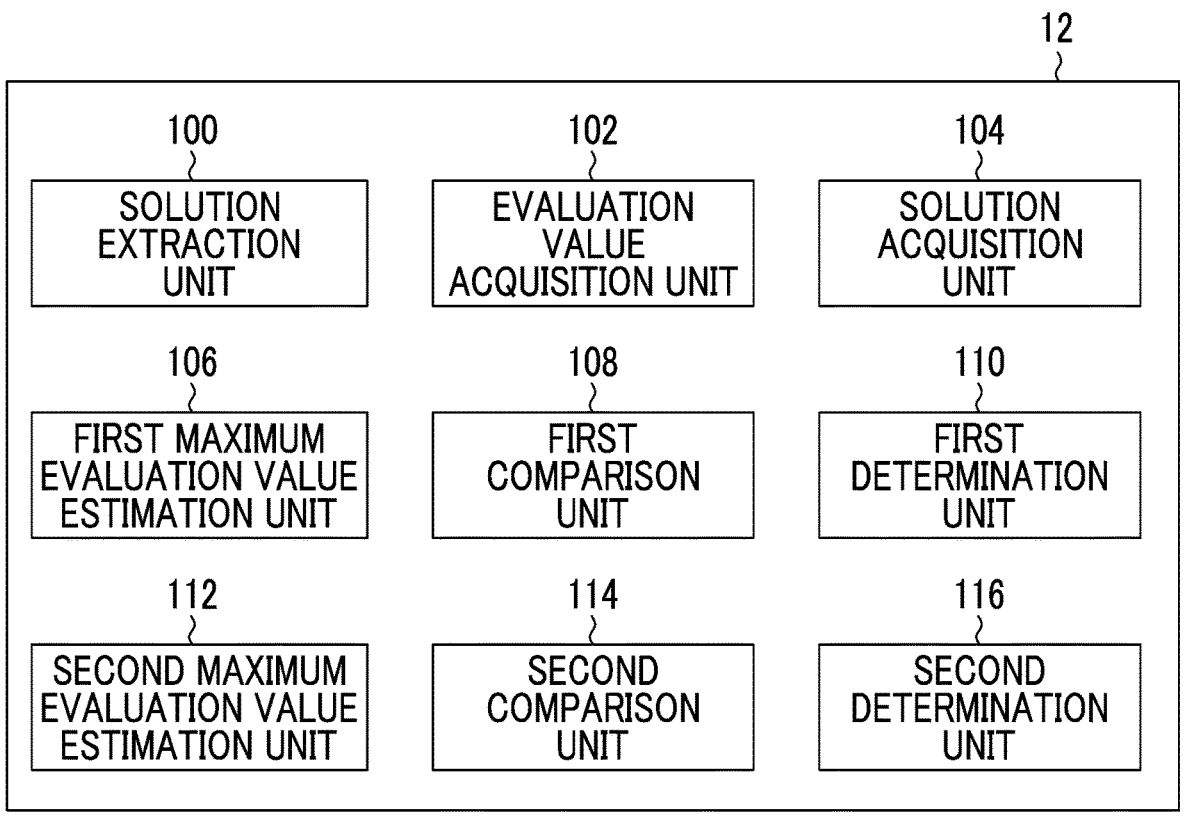
FIG. 16 is a functional block diagram showing a second embodiment of the present invention.

FIG. 16 is a functional block diagram showing functions of the CPU 12 of the optimal solution determination device 10 shown in FIG. 3, which is a functional block diagram showing a second embodiment of the present invention. In FIG. 16, the same reference numerals are given to the same parts as in the first embodiment shown in FIG. 4, and detailed description thereof will not be repeated.

In the second embodiment shown in FIG. 16, a second maximum evaluation value estimation unit 112, a second comparison unit 114, and a second determination unit 116 are additionally provided as main components compared with the first embodiment.

In the first embodiment, even in a case where optimality sufficiency determination of the solution candidate (G_1) is successful, a possibility that a different equivalently probable solution candidate other than the solution candidate (G_1) may be present cannot be excluded.

The second embodiment makes it possible to determine that there is not a different equivalent probable solution candidate other than the solution candidate (G_1).

In FIG. 16, in a case where the optimality sufficiency determination of the solution candidate (graph G_1) is successful according to the first embodiment, then, the solution extraction unit 100 constructs a ZDD for enumerating and indexing solutions that are outside a range of a predetermined distance in the solution space from the graph G_1. The construction of the ZDD may be realized by counting common or non-common edges between the graph G and the graph G_1 in the middle of the construction in the frontier method when the ZDD is constructed. The solution extraction unit 100 uniformly extracts a plurality of second graphs G that are a plurality of second solutions (graphs G) in the solution space of the gene control network and are outside a range of a predetermined distance in the solution space from the graph G_1, by the path enumerating and indexing algorithm using the reconstructed ZDD.

The second maximum evaluation value estimation unit 112 estimates a maximum evaluation value (the second maximum evaluation value W) among evaluation values in a case where solutions of a number that exceeds the number of the plurality of extracted second solutions is assumed, on the basis of the evaluation values respectively corresponding to the plurality of second graphs that are uniformly extracted.

Specifically, the second maximum evaluation value W is estimated by the same method as in the estimation of the first maximum evaluation value Z in the first maximum evaluation value estimation unit 106. That is, when P and Q are natural numbers, respectively, P×Q solutions (a plurality of second graphs G) are uniformly extracted, and an evaluation value S is given to each graph G. Here, P represents a block size, and Q represents the number of blocks. P and Q may be the same as U and V that are uniformly extracted in estimating the first maximum evaluation value Z, or may be different therefrom.

The second maximum evaluation value estimation unit 112 divides P×Q graphs G into Q blocks, and acquires an interval maximum value among evaluation values of U graphs G for each block. Accordingly, Q interval maximum values can be acquired. Further, assuming that the Q interval maximum values follow a generalized extreme value distribution (GEV), the second maximum evaluation value W is obtained by maximum likelihood estimation.

The second comparison unit 114 acquires an evaluation value S_1 corresponding to the solution candidate (graph G_1) acquired by the solution acquisition unit 104 from the evaluation value acquisition unit (second evaluation value acquisition unit) 102, and compares the acquired evaluation value S_1 with the estimated second maximum evaluation value W with a confidence interval.

The second determination unit 116 determines whether the evaluation value S_1 of the graph G_1 exceeds the second maximum evaluation value W (a range of the second maximum evaluation value W with the confidence interval) on the basis of the comparison result of the second comparison unit 104.

Since the first maximum evaluation value Z is obtained by estimating a maximum value in the entire solution space and the second maximum evaluation value W is obtained by estimating a maximum value in a partial space, basically, it is obvious that W≤Z (probabilistically, there may be a case where W>Z in accordance with a sample size, or the like).

Further, in the case of S_1»W (for example, in the case of deviation from the confidence interval), it can be determined that the graph G_1 is a graph assigned the first maximum evaluation value and there is no graph structure capable of describing RNA expression matrix data D at an equivalent or higher level in a range spaced from the graph G_1 in the solution space.

It is necessary to set the range of the predetermined distance to be spaced from the graph G_1 in advance, but the range of the predetermined distance may be set from characteristics of the graph, or may be empirically set. For example, the distance to be spaced may be gradually increased up to a position where S_1»W. For example, an appropriate distance may be repeatedly searched through binary search or the like from a sufficiently large distance setting value with efficiency.

In a case where the distance is zero, W≅Z, which leads to a result that is not different from that of the first embodiment. In a case where the distance is the shortest distance other than zero, only the graph G_1 is not excluded. Accordingly, in a case where a certain degree of distance is not set, it is considered that there is no big difference in the result.

Thus, in a case where the evaluation value S_1 exceeds the second maximum evaluation value W, it can be understood that the graph G_1 is a unique optimal value ("the graph G_1 is necessary and sufficient") in an entire area of the solution space. That is, it can be determined that there is no graph corresponding to an optimal value, other than the graph G_1 obtained through the heuristic search.

Generally, the second embodiment is continuously performed in a case where the determination of the sufficient optimality of the graph G_1 is successful in the first embodiment, but in a case where there is a graph G determined due to a certain reason, the second embodiment may be used as a method for directly comparing solution candidates in a range spaced from the graph G with the graph G.

In the related-art heuristic search, for example, a method for randomly changing initial values, or a method for performing repetitive search by giving noise to data, for example, is also used. However, while this method is based on the heuristic determination method, the present invention is a technique based on a statistical ground.

Figure 17:
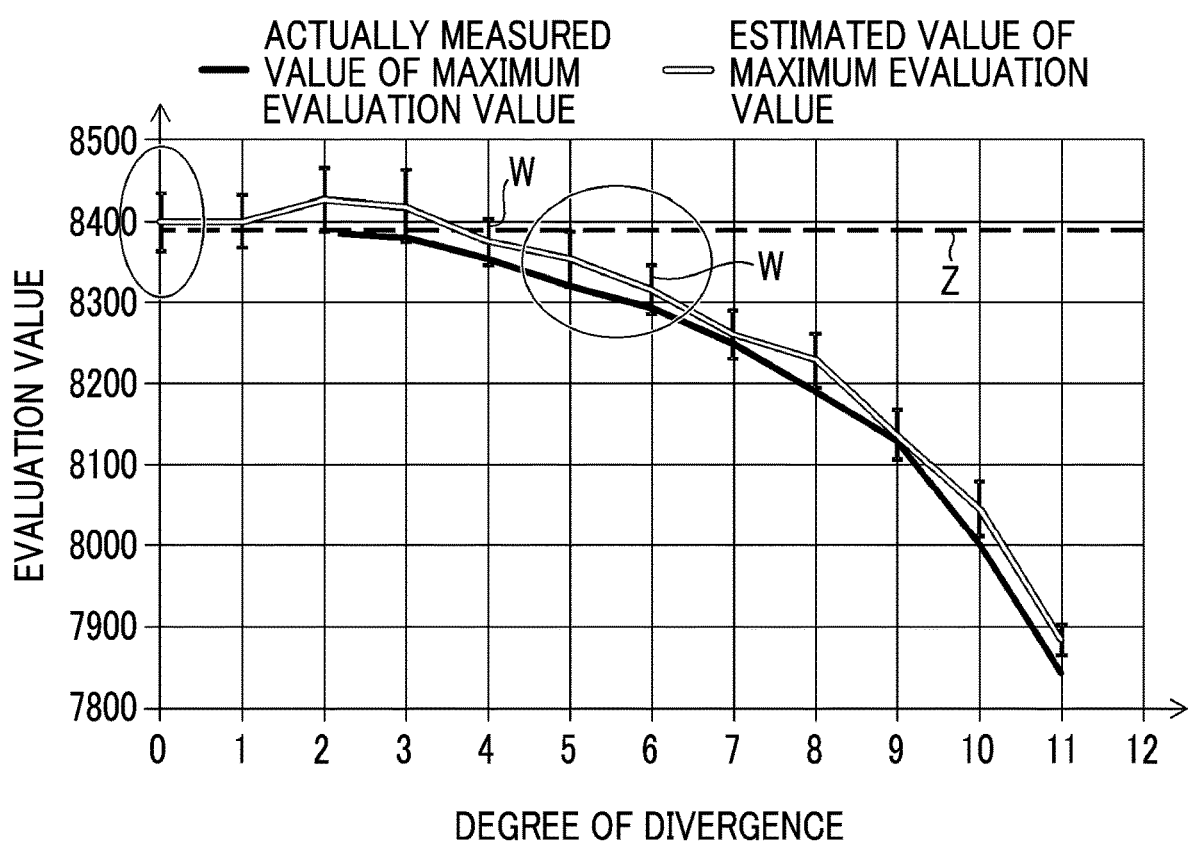
FIG. 17 is a graph showing an example in which the present invention is applied to certain gene control network estimation.

FIG. 17 is a graph showing an example in which the present invention is applied to certain gene control network estimation.

A lateral axis of the graph shown in FIG. 17 represents a degree of divergence (distance), and a longitudinal axis represents an evaluation value. A dashed line represents an arrival evaluation value (first maximum evaluation value Z) for an acquisition graph. Further, a white line represents an estimation value of an optimal value for each degree of divergence.

The "degree of divergence" is generally a distance or an index equivalent to the distance. For example, in a case where a set is expressed as a binary array, the "degree of divergence" may be the Hamming distance. According to problems, a different distance index such as an editing distance, or an index such as a quasi distance or a half distance may be used. Further, a divergence degree index close to these indexes may be defined.

Since an optimal value estimation range in a case where the degree of divergence is zero includes the arrival evaluation value, it is determined that the arrival evaluation value is an optimal value.

Since the value corresponding to the estimation range gradually decreases as the degree of divergence increases and the estimation range (the second maximum evaluation value W) deviates from the arrival evaluation value in a case where the degree of divergence is 5 to 6, it is determined that there is no graph having an evaluation value that is equivalent to or greater than that of the acquisition graph in a range where the degree of divergence is equal to or greater than 5 to 6.

Further, a solid line represents an actual measurement value corresponding to a solution candidate obtained through the heuristic search, which shows that the present invention can accurately estimate an actual state.

<Optimal Solution Determination Method>

First Embodiment

Figure 18:
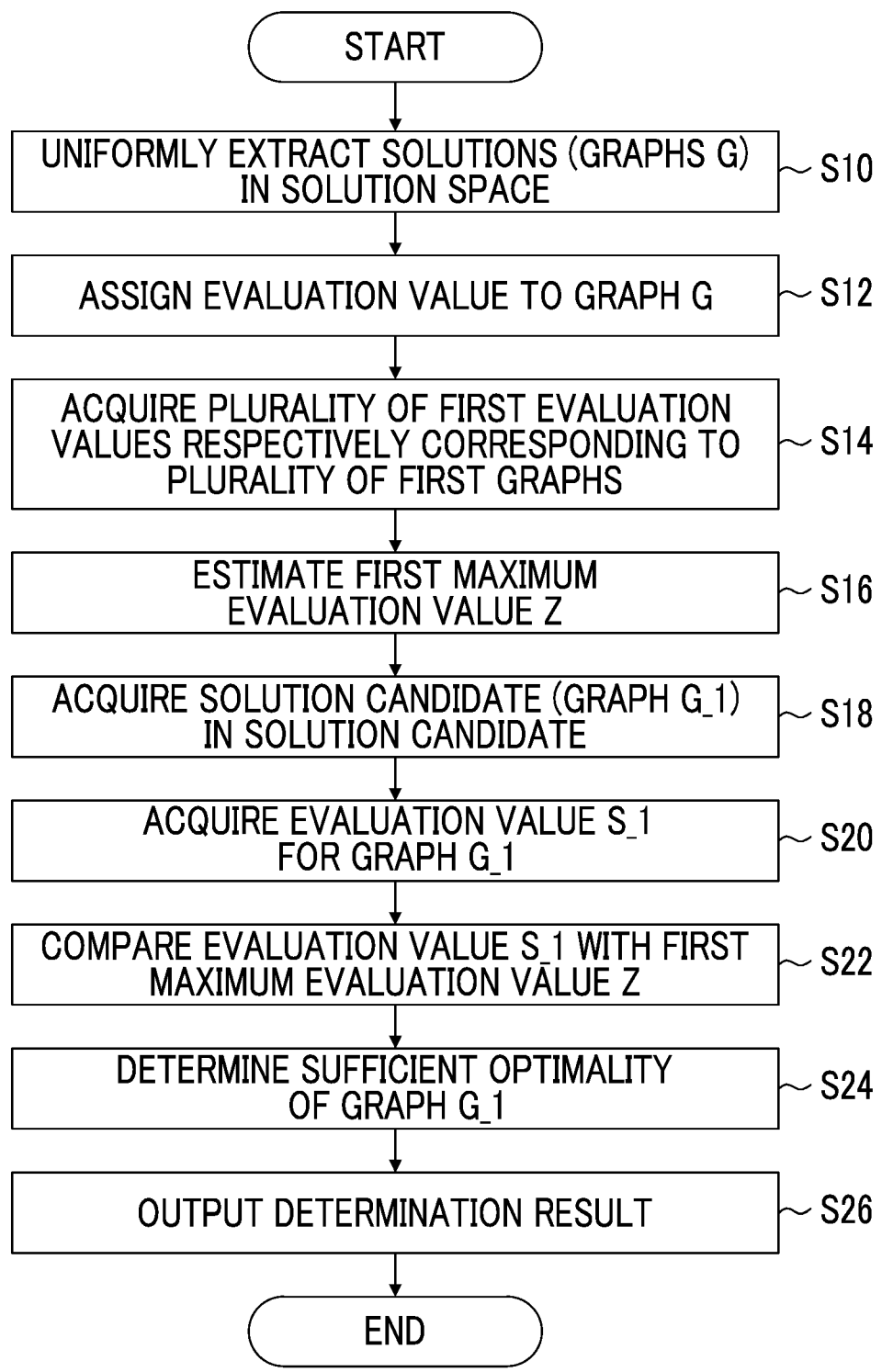
FIG. 18 is a flowchart showing a first embodiment of an optimal solution determination method according to the present invention.

FIG. 18 is a flowchart showing a first embodiment of an optimal solution determination method according to the present invention.

In FIG. 18, the solution extraction unit 100 shown in FIG. 4 uniformly extracts solutions (graphs G) in a solution space of a gene control network that is one of combinatorial optimization problems (step S10 (a first step)). In this example, as described above, the graphs G are uniformly extracted using the above-described path enumerating and indexing algorithm using the ZDD.

Subsequently, the evaluation value acquisition unit 102 assigns evaluation values S to the uniformly extracted graphs G (step S12). For example, an evaluation function S(D, G) obtained by quantifying how much the graphs G can describe RNA expression matrix data D is prepared, and the evaluation value acquisition unit 102 acquires the evaluation values S corresponding to the uniformly extracted graphs G on the basis of the evaluation function S(D, G) and assigns the acquired evaluation values S to the graphs G.

The first maximum evaluation value estimation unit 106 acquires a plurality of first evaluation values S that are assigned to the plurality of uniformly extracted graphs G (the plurality of first solutions) in step S12 (step S14, a second step), and estimates a maximum evaluation value (a first maximum evaluation value) Z among evaluation values in a case where solutions of a number that exceeds the number of the plurality of extracted first solutions G is assumed, on the basis of the plurality of acquired first evaluation values S (step S16, a third step).

Specifically, the plurality of first graphs G are U×V graphs when U and V are respectively natural numbers, and the first maximum evaluation value estimation unit 106 divides the U×V graphs G into V blocks, acquires V interval maximum values of evaluation values of U graphs G for the respective blocks, and estimates a maximum evaluation value (the first maximum evaluation value Z with the confidence interval) using the V interval maximum values by maximum likelihood estimation assuming that the interval maximum values follow a generalized extreme value distribution.

Subsequently, the solution acquisition unit 104 acquires a solution candidate (graph G_1), which is considered to be optimal, acquired through a certain heuristic method for solving an optimization problem of the gene control network (step S18, a fourth step). As the heuristic method, for example, a greedy method, a hill climbing method, a simulated annealing method, taboo search, genetic algorithms, or the like are known, and any one thereof may be used.

An evaluation value S_1 for the acquired graph G_1 is acquired by the evaluation value acquisition unit 102 (first evaluation value acquisition unit) (step S20, a fifth step).

The first comparison unit 108 compares the evaluation value S_1 acquired in step S20 with the first maximum evaluation value Z with the confidence interval estimated in step S16 (step S22, a sixth step).

The first determination unit 110 determines whether the evaluation value S_1 of the graph G_1 is within a range of the first maximum evaluation value Z with the confidence interval on the basis of the comparison result of the first comparison unit 108 (step S24, a seventh step). That is, the first determination unit 110 determines that the graph G_1 satisfies a sufficient condition as an optimal value in a case where the evaluation value S_1 is within the confidence interval of the first maximum evaluation value with the confidence interval.

The determination result in the first determination unit 110 is displayed on the monitor device 28 shown in FIG. 3, is stored in the hard disk device 20, or is print-output through a printer (not shown) (step S26, an eighth step). The determination result in the first determination unit 110 is not limited to the presence or absence of sufficient optimality. In a case where the sufficient optimality is not present, a difference between the evaluation value S_1 and the first maximum evaluation value Z is converted into a distance in a solution space, and it may be determined how far the currently estimated graph G_1 is spaced from a true optimal solution (solution corresponding to the first maximum evaluation value Z).

According to the first embodiment, it is possible to determine whether the solution candidate (graph G_1) searched by heuristic search has sufficient optimality as a true optimal value. Further, even in a case where the determination of the sufficient optimality is not successful, it is suggested that another optimal solution is present since the heuristic search is not sufficient. Further, in accordance with the degree of failure, it may be asserted that the solution candidate is close to the optimal solution to some extent, or the solution candidate may be used while noting another optimal solution is present. That is, regardless of the success or failure of the sufficient optimality, information on the sufficient optimality determination is useful.

[Modification Example of the First Embodiment]

In a case where the sufficient optimality determination based on the present procedure is not successful, the same heuristic search may be repeated by different settings, or the like, but a method for preparing a plurality of searches for performing heuristic search in advance (a first search method and a second search method, for example) and switching the plurality of search methods in use.

For example, as the heuristic methods, a first search method in which computation cost is small (search time is short) and solution accuracy is low and a second search method in which computation cost is larger than that in the first search method (search time is long) and solution accuracy is higher than that in the first search method are provided. Then, sufficient optimality of a first solution candidate (graph G_1) that is first searched by the first search method is determined, and only in a case where the determination of the sufficient optimality is not successful, sufficient optimality of a second solution candidate (graph G_1) that is searched by the second search method is determined.

The switching between the search methods may be switching between the same heuristic search methods, or may be switching to an approximation algorithm for which similarity is guaranteed to some extent or a method for calculating an exact solution. Further, three or more search methods may be prepared, and then, may be sequentially switched. The switching between the search methods is not limited to the level of the methods, and may be realized by convergence determinations in the same search method, or the like. For example, in a search method for enhancing accuracy by repetitive search, a predetermined number of times of search results may be determined by the first maximum evaluation value Z, and the search may be repeated until arriving within the confidence interval of the first maximum evaluation value Z.

Further, in this case, the first maximum evaluation value Z for determining sufficient optimality may be acquired in advance.

Second Embodiment

Figure 19:
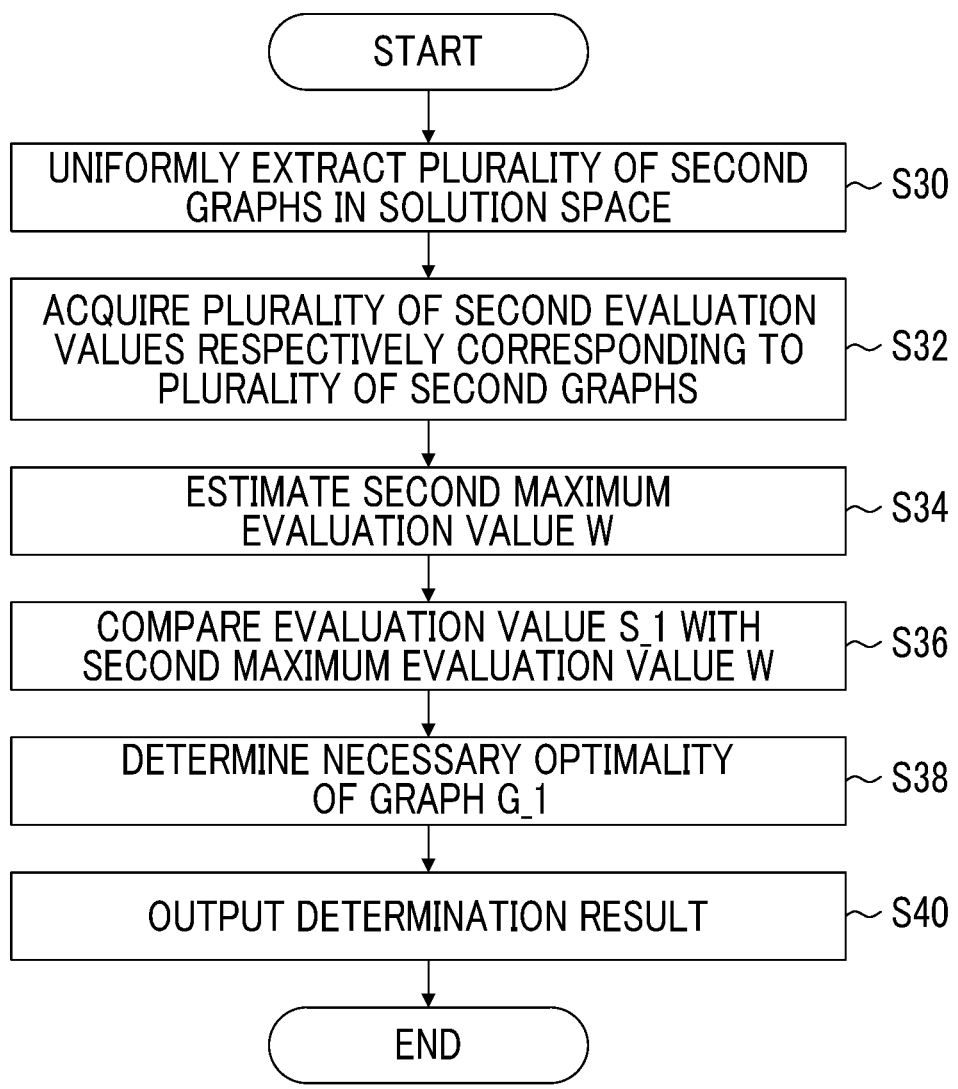
FIG. 19 is a flowchart showing a second embodiment of the optimal solution determination method according to the present invention, which is particularly a flowchart showing a necessary optimality determination process performed after sufficient optimality determination is successful.

FIG. 19 is a flowchart showing a second embodiment of the optimal solution determination method according to the present invention, and particularly, shows a process of necessary optimality determination performed after the sufficient optimality determination according to the first embodiment shown in FIG. 18 is successful.

In FIG. 19, the solution extraction unit 100 (a second solution extraction unit) shown in FIG. 16 uniformly extracts a plurality of (plurality of second) graphs G that are a plurality of second graphs G in the solution space of the gene control network and are outside a range of a predetermined distance in the solution space from the graph G_1 that succeeds in the sufficient optimality determination (step S30, a ninth step). The uniform extraction of the plurality of second graphs G can be performed by constructing a ZDD for enumerating and indexing solutions that are outside a range of a predetermined distance in the solution space from the graph G_1 and executing a path enumerating and indexing algorithm using the constructed ZDD.

Subsequently, the evaluation value acquisition unit 102 acquires evaluation values S, respectively, with respect to the plurality of uniformly extracted second graphs G (step S32, a tenth step). The acquisition of the evaluation values S for the graphs G may be similarly performed in step S12 of the first embodiment shown in FIG. 18.

Then, the second maximum evaluation value estimation unit 112 estimates a maximum evaluation value (a second maximum evaluation value) W among evaluation values in a case where solutions of a number that exceeds the number of the plurality of extracted second solutions G is assumed, on the basis of the plurality of second evaluation values S acquired in step S32 (step S34, an eleventh step).

Specifically, the plurality of second graphs G are P×Q graphs when P and Q are natural numbers, respectively. The second maximum evaluation value estimation unit 112 divides the P×Q graphs G into Q blocks, acquires Q interval maximum values of evaluation values of P graphs G for the respective blocks, and estimates the maximum evaluation value (the second maximum evaluation value W with the confidence interval) using the Q interval maximum values by maximum likelihood estimation, assuming that the interval maximum value follows a generalized extreme value distribution.

Subsequently, the second comparison unit 114 compares an evaluation value S_1 of the graph G_1 that succeeds in the sufficient optimality determination with the second maximum evaluation value W with the confidence interval estimated in step S34 (step S36, a twelfth step).

The second determination unit 116 determines whether the evaluation value S_1 of the graph G_1 exceeds a range of the second maximum evaluation value W with the confidence interval on the basis of the comparison result in the second comparison unit 114 (step S38, a thirteenth step). That is, in a case where the evaluation value S_1 exceeds the range of the second maximum evaluation value with the confidence interval, the second determination unit 116 determines that another solution equivalent to the graph G_1 is not present and the graph G_1 satisfies a necessary condition as a unique optimal value (necessary optimality is present).

The determination result in the second determination unit 116 is displayed on the monitor device 28 shown in FIG. 3, is stored in the hard disk device 20, or is print-output through a printer (not shown) (step S40, a fourteenth step).

According to the second embodiment, in a case where the solution candidate (graph G_1) searched by the heuristic research succeeds in sufficient optimality determination as a true optimal value, since the necessary optimality of the graph G_1 is determined, it is possible to confirm that there is no solution having an equivalent evaluation value in a solution space spaced from the searched graph G_1.

Third Embodiment

A third embodiment of the optimal solution determination method according to the present invention includes a process in a case where the sufficient optimality determination is not successful in the second embodiment shown in FIG. 19.

That is, in a case where the sufficient optimality determination is not successful, in step S30 shown in FIG. 19 (a fifteenth step), the predetermined range from the graph G_1 is enlarged in the solution space, and a plurality of third solutions G_3 (a plurality of third solutions) in a solution space outside the enlarged predetermined range are uniformly extracted.

Further, acquisition of evaluation values of the plurality of third solutions respectively corresponding to the plurality of third groups G extracted in the solution space outside the enlarged predetermined range (step S32, a sixteenth step), estimation of a third maximum evaluation value W in a case where solutions of a number that exceeds the number of the plurality of third graphs G are assumed, on the basis of the plurality of third evaluation values (step S34, a seventeenth step), comparison of the evaluation value S_1 of the graph G_1 and the third maximum evaluation value W (step S36), determination of necessary optimality of the graph G_1 (step S38, an eighteenth step), and the like are executed again.

In a case where the sufficient optimality determination is not successful, the process of enlarging the predetermined range may be repeated plural times until succeeding in the sufficient optimality determination to gradually enlarge the predetermined range.

Fourth Embodiment

A fourth embodiment of the optimal solution determination method according to the present invention includes other processes in a case where the sufficient optimality determination is not successful in the second embodiment shown in FIG. 19.

Figure 20:
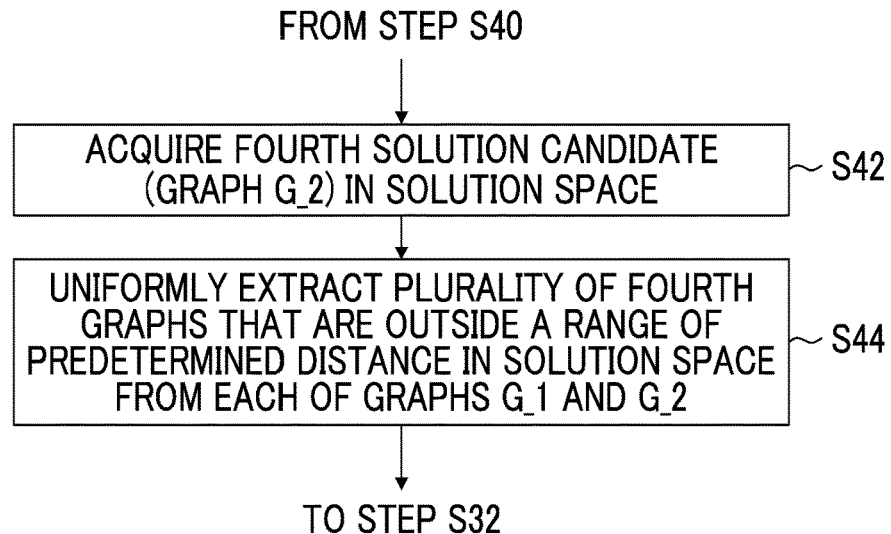
FIG. 20 is a flowchart showing main units of a fourth embodiment of the optimal solution determination method according to the present invention.

In a case where the sufficient optimality determination is not successful (that is, in a case where a determination result indicating that the evaluation value S_1 of the graph G_1 does not exceed the second maximum evaluation value W is output), as shown in FIG. 20, a fourth solution candidate (graph G_2) that is spaced from the graph G_1 in the solution space by a predetermined distance, which is a graph G_2 having an evaluation value S_2 corresponding to the second maximum evaluation value W, is acquired (step S42, a nineteenth step).

The acquisition of the graph G_2 is performed by executing heuristic search of the solution candidate (graph G_2) in a solution space range outside a range of a predetermined distance from the graph G_1 and acquiring the graph G_2 in which the evaluation value S_2 thereof becomes W≅Z.

Then, instead of step S30 shown in FIG. 19, a plurality of fourth solutions that are outside a range of a predetermined distance in the solution space from each of the graph G_1, and the graph G_2 are uniformly extracted (step S44, a twentieth step).

Then, the procedure proceeds to step S32 shown in FIG. 19, acquisition of a plurality of fourth evaluation values respectively corresponding to the plurality of fourth solutions extracted in the solution space that are outside the predetermined range enlarged as described above (step S32, a twenty first step), estimation of a fourth maximum evaluation value W in a case where solutions of a number that exceeds the number of the plurality of fourth solutions G are assumed, on the basis of the plurality of fourth evaluation values (step S34, a twenty second step), comparison of the evaluation value S_1 of the graph G_1 and the fourth maximum evaluation value W (step S36), determination of necessary optimality of the graph G_1 is determined (step S38, a twenty third step), and the like are executed again.

Further, in a case where the sufficient optimality determination is not successful again, the determination of the necessary optimality is repeatedly performed by newly adding a graph G_3 or the like and estimating a new fourth maximum evaluation value W.

The predetermined range (meaningful distance) is determined from a request from a combinatorial optimization problem. For example, in the case of the gene control network, since a distance d means the number of different edges, it may be analyzed by the number of errors of edges allowed in an action mechanism solution or the like. In a case where it is expected that a total number of edges is about N, since an index indicating a wrong answer rate is considered to be d/N, for example, in a case where a wrong answer rate of 5% is allowed and it is expected that N is 100, d=5 may be set, for example.

Fifth Embodiment

There is a case where solutions cannot be uniformly extracted from the entire solution space. There is a case where a uniformly extracting unit cannot be secured, such as a case where the ZDD of the entire solution space cannot be constructed, for example.

A fifth embodiment of the optimal solution determination method according to the present invention capable of being applied to such a case will be described.

Figure 21:
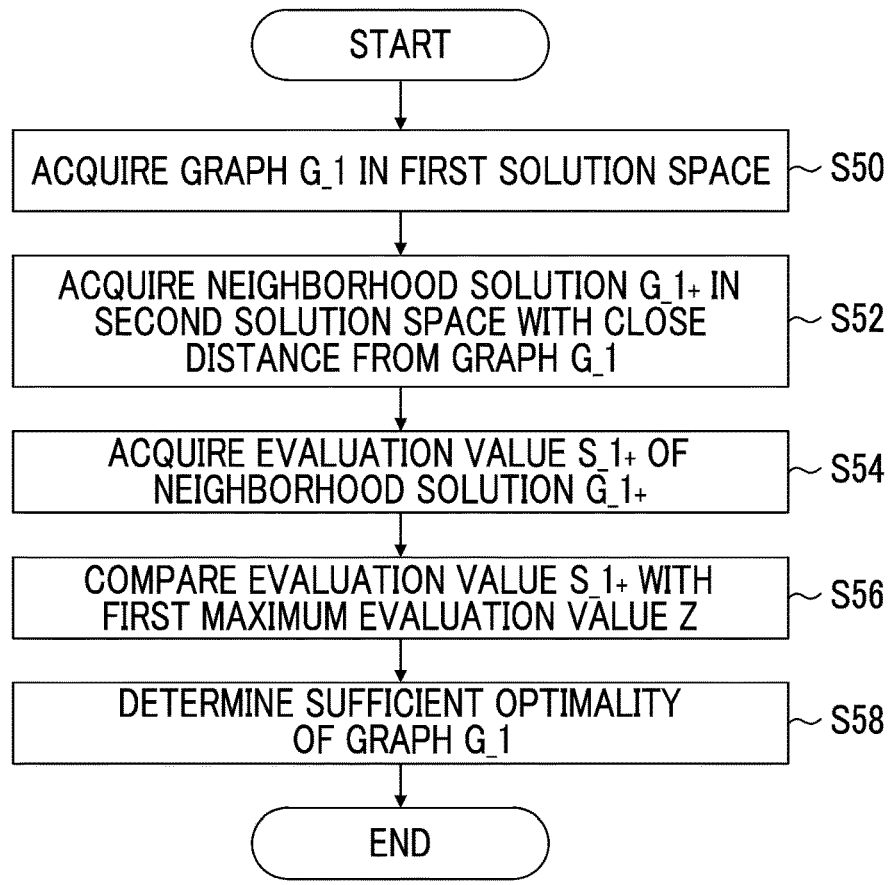
FIG. 21 is a flowchart showing a fifth embodiment of the optimal solution determination method according to the present invention.

FIG. 21 is a flowchart showing the fifth embodiment of the optimal solution determination method according to the present invention.

First, in a case where the ZDD cannot be constructed only using the constraint condition C, a stricter constraint condition C+ capable of constructing the ZDD is considered. For example, in a graph problem, in a case where the constraint condition C is only "acyclic", a method for assigning "spanning forest" may be considered, for example. It is assumed that the solution space of the combinatorial optimization problem includes a first solution space in the constraint condition C (first constraint condition) and a second solution space in the constraint condition C+ (second constraint condition).

In FIG. 21, the first solution candidate (graph G_1) is acquired from solutions (graph {G} in the constraint condition C) that belong to the first solution space (step S50, a twenty fourth step). In the first solution space, even in a case where the ZDD or the like cannot be constructed, it is possible to search the graph G_1 using the heuristic method, or the like.

Subsequently, solutions in the second solution space ({$G_+$} in the constraint condition $C_+$) are enumerated, and a neighborhood solution $G\_1_+$ in the constraint condition $C_+$ of the graph G_1 acquired in step S50 is searched (step S52, a twenty eighth step). For example, since the ZDD in the constraint condition $C_+$ can be described, the ZDD may be constructed by adding a condition that "a distance in the solution space from G_1 is to be within a predetermined range" to the constraint condition $C_+$, and the neighborhood solution $G\_1_+$ may be searched by selecting a solution candidate having a minimum distance.

Then, an evaluation value $S\_1_+$ of the neighborhood solution $G\_1_+$ is acquired (step S54, a twenty ninth step). The acquisition of the evaluation value $S\_1_+$ with respect to the neighborhood solution $G\_1_+$ can be performed in a similar way to step S12 of the first embodiment shown in FIG. 18.

The evaluation value $S\_1_+$ of the neighborhood solution $G\_1_+$ acquired in step S54 is compared with a fifth maximum evaluation value Z with a confidence interval (step S56). The fifth maximum evaluation value Z may be estimated by the above-described method on the basis of the uniform extraction of the graph "{$G_+$}" in the constraint condition $C_+$ in the second solution space. That is, a plurality of solutions in the second solution space are uniformly extracted as a plurality of fifth solutions (graphs {$G_+$} in the constraint condition $C_+$) (a twenty fifth step), a plurality of fifth evaluation values respectively corresponding to the plurality of fifth solutions are acquired (a twenty sixth step), and a fifth maximum evaluation value is estimated in a case where solutions of a number that exceeds the number of the plurality of fifth solutions are assumed, on the basis of the plurality of acquired fifth evaluation values (a twenty seventh step).

Further, sufficient optimality of the graph G_1 is determined on the basis of the comparison result of the evaluation value $S\_1_+$ of the neighborhood solution $G\_1_+$ and the first maximum evaluation value Z with the confidence interval (step S58, a thirtieth step). That is, it is determined whether the evaluation value $S\_1_+$ is within the confidence interval of the first maximum evaluation value Z, and in a case where the evaluation value $S\_1_+$ is within the confidence interval of the first maximum evaluation value Z so that the sufficient optimality of the neighborhood solution $G\_1_+$ is present, it is determined that the graph G_1 also has sufficient optimality. It is because in a case where the neighborhood solution $G\_1_+$ is optimal, in the least, it is possible to guarantee that "a solution is found out at a place closest from an optimal solution in a case where "a stricter condition is given".

Figure 22:
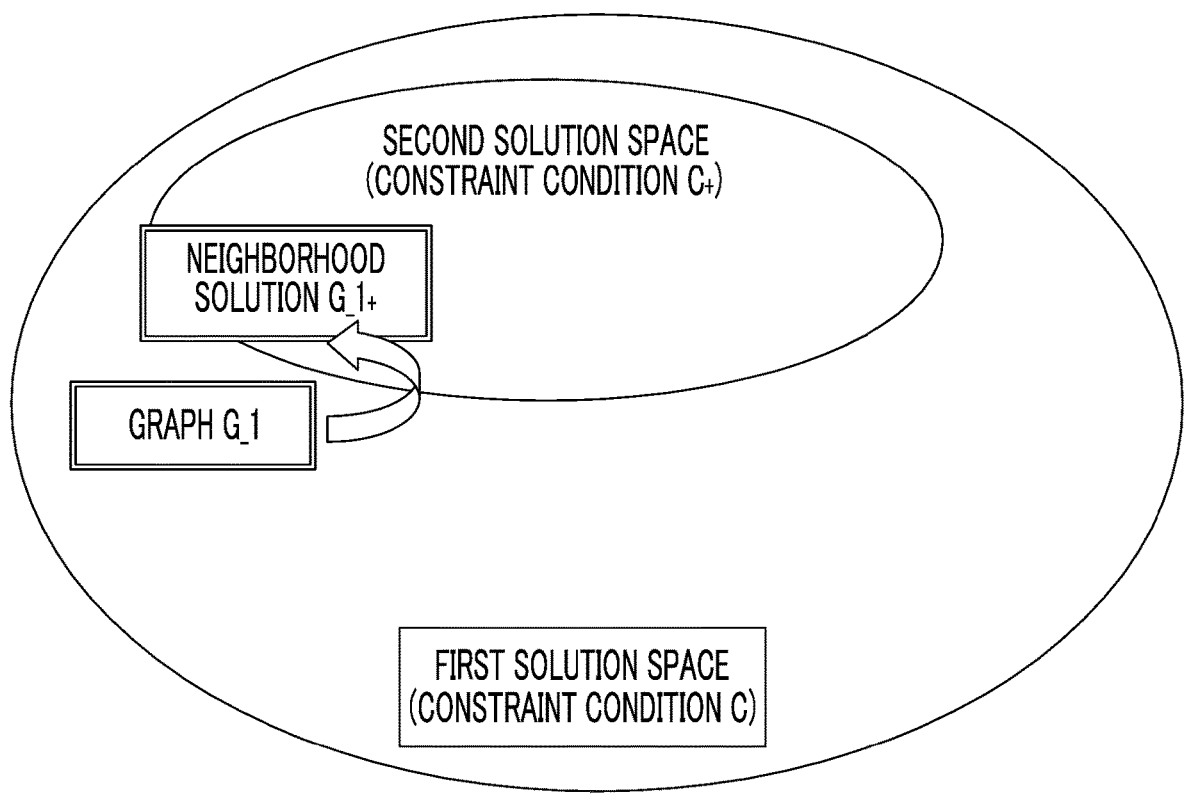
FIG. 22 is a diagram schematically showing a first solution space in a constraint condition C and a second solution space in a constraint condition $C_+$.

FIG. 22 is a diagram schematically showing the first solution space in the constraint condition C and the second solution space in the constraint condition $C_+$. In a case where optimality determination of the graph G_1 searched by the heuristic method or the like in the first solution space in the constraint condition C incapable of constructing the ZDD is performed, the neighborhood solution $G\_1_+$ in the second solution space in the stricter constraint condition $C_+$ capable of constructing the ZDD is searched, optimality determination of the neighborhood solution $G\_1_+$ (a solution at a minimum distance in a range of a predetermined distance from the graph G_1 in the solution space) is substitutively used to perform the optimality determination of the graph G_1.

The second solution space becomes "$C_+ \subseteq C$" since a constraint is added (FIG. 22). It is because a constraint included in the constraint condition C is a model precondition or a valid constraint according to prior knowledge, and thus, should not be basically excluded. It is preferable that an added constraint is assumed to have validity to some extent with respect to a problem by prior knowledge or the like (but it is not essential that complete validity is secured).

However, in a case where exclusion of the constraint makes search easy and there is not a severe damage in validity even though the constraint is excluded, the constraint such as "$C_+ \subseteq C$", that is, release of the constraint may be considered.

In any case, a difference between the constraint conditions C and $C_+$ and a minimum distance d between the graph G_1 and the neighborhood solution $G\_1_+$ represent the degree of divergence between the neighborhood solution $G\_1_+$ that is substitutively used and an arrival solution to be actually used. With respect to the search of the neighborhood solution $G\_1_+$, in a case where it can be said that the search is being performed with respect to the neighborhood of the minimum distance d of an arrival solution, for example, using the heuristic method, it is considered that there is not a problem in practical use. On the other hand, the influence of the difference between the constraint conditions C and $C_+$ depends on how much the evaluation value is changed due to the difference. In a constraint condition that such a large influence is not given to the evaluation value, in a case where the minimum distance d is in a valid range, it may be considered that optimality determination of the neighborhood solution $G\_1_+$ is substitutively used and reliability in performing the optimality determination of the graph G_1 is high. With this configuration, it is possible to achieve effects of the present invention with respect to wider combinational optimization problems.

[Others]

The optimal solution determination device 10 of this embodiment is merely exemplary, and the present invention may be applied to different configurations. Respective functional configurations may be appropriately realized by unspecified hardware, software, or a combination thereof. For example, the present invention may be applied to an optimal solution determination program for causing a computer to execute the processes in the respective units of the above-mentioned optimal solution determination device 10, and a computer-readable recording medium (non-temporary recording medium) on which the optimal solution determination program is recorded.

Further, in this embodiment, for example, a hardware structure of processing units that execute a variety of processes, such as the solution extraction unit 100, the evaluation value acquisition unit 102, the solution acquisition unit 104, the first maximum evaluation value estimation unit 106, the first comparison unit 108, the first determination unit 110, and the like corresponds to a variety of processors as follows. The variety of processors include a central processing unit (CPU) that is a general-purpose processor that functions as a variety of processing units by executing software (program), a programmable logic device (PLD) that is a processor capable of changing a circuit configuration after manufacturing, such as a field programmable gate array (FPGA), an exclusive electric circuit that is a processor that has a circuit configuration that is exclusively designed for executing a specific process, such as an application specific integrated circuit (ASIC), or the like.

A processing unit may be configured as one processor among the variety of processors, or may be configured as the same or different kinds of two or more processors (for example, a combination of a plurality of FPGAs or a combination of a CPU and an FPGA). Further, a plurality of processing units may be configured as one processor. As an example in which the plurality of processing units are configured as one processor, first, as represented as a client or a server computer, there is a type in which one process is configured by a combination of one or more CPUs and software and the process functions as the plurality of processing units is used. Second, as represented as a system on chip (SoC) or the like, there is a type in which a processor that realizes entire functions of a system including the plurality of processing units by one integrated circuit (IC) chip is used. As described above, the variety of processing units is configured as a hardware structure using the above-mentioned one or more processors of the variety of processors.

Further, the hardware structure of the variety of processors is, more specifically, an electric circuitry in which circuit elements such as a semiconductor device are combined.

In addition, the present invention provides an optimal solution determination device that includes a processor, in which the processor uniformly extracts a plurality of solutions in a solution space of a combinatorial optimization problem as a plurality of first solutions, acquires a plurality of first evaluation values respectively corresponding to the plurality of first solutions that are uniformly extracted, estimates, as a first maximum evaluation value, a maximum evaluation value in a case where solutions of a number that exceeds the number of the plurality of first solutions are assumed, on the basis of the plurality of acquired first evaluation values, acquires at least one solution among solutions that belong to the solution space as a solution candidate, and determines whether an evaluation value corresponding to the acquired solution candidate is within a confidence interval of the first maximum evaluation value.

Further, the present invention is not limited to the above-described embodiments, and various modifications may be made in a range without departing from the concept of the present invention.

EXPLANATION OF REFERENCES

10: optimal solution determination device
12: CPU
14: main memory
16: graphic board
18: communication interface
20: hard disk device
22: CD-ROM driver
24: keyboard controller
26: mouse controller
28: monitor device
30: keyboard
32: mouse
40: database
50: network
100: solution extraction unit
102: evaluation value acquisition unit
104: solution input unit
106: first maximum evaluation value estimation unit
108: first comparison unit
110: first determination unit
112: second maximum evaluation value estimation unit
114: second comparison unit
116: second determination unit
Z: first maximum evaluation value
W: second maximum evaluation value

What is claimed is:

1. An optimal solution determination method for determining optimality of a solution in a combinatorial optimization problem of a gene control network by executing processes of following steps by a computer, comprising:
a first step of uniformly extracting a plurality of solutions in a solution space of the combinatorial optimization problem as a plurality of first solutions using a data structure obtained by contracting combinable patterns to form the data structure to be enumerated and indexed, or random generation;
a second step of acquiring, based on an evaluation function, a plurality of first evaluation values respectively corresponding to the plurality of first solutions that are uniformly extracted in the first step;
a third step of estimating a maximum evaluation value in a case where a number of solutions that exceeds the number of the plurality of first solutions are assumed, on the basis of the acquired plurality of first evaluation values, and setting the estimated maximum evaluation value as a first maximum evaluation value;
a fourth step of acquiring at least one solution among solutions that belong to the solution space as a solution candidate by a heuristic search;
a fifth step of acquiring an evaluation value corresponding to the solution candidate based on the evaluation function;
a sixth step of determining whether the evaluation value corresponding to the solution candidate acquired in the fifth step is within a confidence interval of the first maximum evaluation value; and
a seventh step of setting the solution candidate as a first optimal solution for a graph describing an RNA expression matrix data in a case where it is determined in the sixth step that the evaluation value corresponding to the solution candidate is within the confidence interval of the first maximum evaluation value,
thereby producing a medicine which is offered to a human body, by acquiring an action mechanism of the medicine based on the first optimal solution for the graph describing the RNA expression matrix,
wherein the plurality of first solutions are U×V solutions when U and V are respectively natural numbers, and
wherein in the third step, the U×V solutions are divided into V blocks, V division maximum values of evaluation values of U solutions are acquired for the respective blocks, and the first maximum evaluation value is estimated using the V division maximum values assuming that the interval maximum values follow a generalized extreme value distribution.

2. The optimal solution determination method according to claim 1, further comprising:
an eighth step of outputting a determination result in the seventh step.

3. The optimal solution determination method according to claim 1,
wherein a first search method in which computation cost is small and solution accuracy is low and a second search method in which computation cost is larger than that in the first search method and solution accuracy is higher than that in the first search method are provided, and
wherein in the fourth step, a first solution candidate that is first searched by the first search method is input, and only in a case where an evaluation value of the first solution candidate is not within a range of the first maximum evaluation value, a second solution candidate that is searched by the second search method is input.

4. The optimal solution determination method according to claim 1, further comprising:
a ninth step of uniformly extracting a plurality of solutions that are solutions in the solution space and are outside a range of a predetermined distance in the solution space from the first optimal solution, as a plurality of second solutions using the data structure obtained by contracting combinable patterns to form the data structure to be enumerated and indexed, or random generation;
a tenth step of acquiring, based on an evaluation function, a plurality of second evaluation values respectively corresponding to the plurality of second solutions;
an eleventh step of estimating a maximum evaluation value in a case where solutions of a number that exceeds the number of the plurality of second solutions are assumed, on the basis of the plurality of second evaluation values, and setting the estimated maximum evaluation value as a second maximum evaluation value;
a twelfth step of acquiring an evaluation value of the first optimal solution; and
a thirteenth step of determining whether the evaluation value of the first optimal solution exceeds the second maximum evaluation value,
wherein the plurality of second solutions are P×Q solutions when P and Q are respectively natural numbers, and
wherein in the eleventh step, the P×Q solutions are divided into Q blocks, Q interval maximum values of evaluation values of P solutions for the respective blocks are acquired, and the second maximum evaluation value is estimated using the Q interval maximum values assuming that the interval maximum values follow a generalized extreme value distribution.

5. The optimal solution determination method according to claim 4, further comprising:
a fourteenth step of outputting a determination result in the thirteenth step.

6. The optimal solution determination method according to claim 4, further comprising:
a fifteenth step of enlarging the range of the predetermined distance in a case where it is determined in the thirteenth step that the evaluation value of the first optimal solution does not exceed the second maximum evaluation value, and uniformly extracting a plurality of solutions outside the enlarged range of the predetermined distance as a plurality of third solutions;
a sixteenth step of acquiring a plurality of third evaluation values respectively corresponding to the plurality of third solutions;
a seventeenth step of estimating a maximum evaluation value in a case where solutions of a number that exceeds the number of the plurality of third solutions are assumed, on the basis of the plurality of third evaluation values, and setting the estimated maximum evaluation value as a third maximum evaluation value; and
an eighteenth step of determining whether the evaluation value of the first optimal solution exceeds the third maximum evaluation value.

7. The optimal solution determination method according to claim 4, further comprising:
a nineteenth step of acquiring a fourth solution candidate that is a solution in the solution space and is spaced from the first optimal solution by a predetermined distance in a case where it is determined in the thirteenth step that the evaluation value of the first optimal solution does not exceed the second maximum evaluation value;
a twentieth step of uniformly extracting a plurality of fourth solutions that are outside a range of a predetermined distance in the solution space from each of the first optimal solution and the fourth solution candidate, in the solution space;
a twenty first step of acquiring a plurality of fourth evaluation values respectively corresponding to the plurality of fourth solutions;
a twenty second step of estimating a maximum evaluation value in a case where solutions of a number that exceeds the number of the plurality of fourth solutions are assumed, on the basis of the plurality of fourth evaluation values, and setting the estimated maximum evaluation value as a fourth maximum evaluation value; and
a twenty third step of determining whether the evaluation value of the first optimal solution exceeds the fourth maximum evaluation value.

8. The optimal solution determination method according to claim 1,
wherein the solution space includes a first solution space in a first constraint condition and a second solution space in a second constraint condition,
the method further comprising:
a twenty fourth step of acquiring the first solution candidate that belongs to the first solution space;
a twenty fifth step of uniformly extracting a plurality of solutions in the second solution space as a plurality of fifth solutions;
a twenty sixth step of acquiring a plurality of fifth evaluation values respectively corresponding to the plurality of fifth solutions;
a twenty seventh step of estimating a maximum evaluation value in a case where solutions of a number that exceeds the number of the plurality of fifth solutions are assumed, on the basis of the plurality of acquired fifth evaluation values, and setting the estimated maximum evaluation value as a fifth maximum evaluation value;
a twenty eighth step of acquiring a solution that is a solution candidate in the second solution space and is at a close distance in the solution space from the first solution candidate acquired in the twenty fourth step as a neighborhood solution;
a twenty ninth step of acquiring an evaluation value of the neighborhood solution; and
a thirtieth step of determining whether the evaluation value of the neighborhood solution is within a confidence interval of the fifth maximum evaluation value.

9. The optimal solution determination method according to claim 1,
wherein the first step includes calculating a total number of solutions in the solution space using a data structure obtained by contracting combinable patterns, using at least one of a step of identifying whether to confirm non-suitability using a part of combinations without considering the remaining combinations, among the combinable patterns in the combinatorial optimization problem to reduce patterns to be identified or a step of extracting a common part of a pattern group with a difference in only a part of combinations among the combinable patterns and sharing the remaining combinations to reduce patterns to be identified, and by enumerating and indexing the contracted combinable patterns, generating a random number that is equal to or smaller than the calculated total number, and extracting solutions corresponding to patterns specified by the generated random number.

10. The optimal solution determination method according to claim 1,
wherein the combinatorial optimization problem is a combinatorial optimization problem of a gene control network.

11. A non-transitory computer readable recording medium which records a program that causes a computer to execute a process for determining optimality of a solution in a combinatorial optimization problem of a gene control network, comprising:
a first step of uniformly extracting a plurality of solutions in a solution space of the combinatorial optimization problem as a plurality of first solutions using a data structure obtained by contracting combinable patterns to form the data structure to be enumerated and indexed, or random generation;
a second step of acquiring, based on an evaluation function, a plurality of first evaluation values respectively corresponding to the plurality of first solutions that are uniformly extracted in the first step;
a third step of estimating a maximum evaluation value in a case where a number of solutions that exceeds the number of the plurality of first solutions are assumed, on the basis of the acquired plurality of first evaluation values, and setting the estimated maximum evaluation value as a first maximum evaluation value;
a fourth step of acquiring at least one solution among solutions that belong to the solution space as a solution candidate by a heuristic search;
a fifth step of acquiring an evaluation value corresponding to the solution candidate based on the evaluation function;
a sixth step of determining whether the evaluation value corresponding to the solution candidate acquired in the fifth step is within a confidence interval of the first maximum evaluation value; and
a seventh step of setting the solution candidate as a first optimal solution for a graph describing an RNE expression matrix data in a case where it is determined in the sixth step that the evaluation value corresponding to the solution candidate is within the confidence interval of the first maximum evaluation value,
thereby producing a medicine which is offered to a human body, by acquiring an action mechanism of the medicine based on the first optimal solution for the graph describing the RNA expression matrix,
wherein the plurality of first solutions are U×V solutions when U and V are respectively natural numbers, and
wherein in the third step, the U×V solutions are divided into V blocks, V division maximum values of evaluation values of U solutions are acquired for the respective blocks, and the first maximum evaluation value is estimated using the V division maximum values assuming that the interval maximum values follow a generalized extreme value distribution.

12. An optimal solution determination device that includes a processor and a memory storing an optimal solution determination program and determines optimality of a solution in a combinatorial optimization problem of a gene control network by executing the optimal solution determination program by the processor,
wherein the processor functions as:
a solution extraction unit that uniformly extracts a plurality of solutions in a solution space of the combinatorial optimization problem as a plurality of first solutions using a data structure obtained by contracting combinable patterns to form the data structure to be enumerated and indexed, or random generation;
a first evaluation value acquisition unit that acquires, based on an evaluation function, a plurality of first evaluation values respectively corresponding to the plurality of first solutions that are uniformly extracted;
a first maximum evaluation value estimation unit that estimates a maximum evaluation value in a case where a number of solutions that exceeds the number of the plurality of first solutions are assumed, on the basis of the plurality of acquired first evaluation values, and sets the estimated maximum evaluation value as a first maximum evaluation value;
a solution acquisition unit that acquires at least one solution among solutions that belong to the solution space as a solution candidate by a heuristic search; and
a first determination unit that acquires an evaluation value corresponding to the solution candidate from the first evaluation value acquisition unit based on the evaluation function, determines whether the evaluation value corresponding to the acquired solution candidate is within a confidence interval of the first maximum evaluation value, and sets the solution candidate as a first optimal solution for a graph describing an RNA expression matrix data in a case where it is determined that the evaluation value corresponding to the solution candidate is within the confidence interval of the first maximum evaluation value,
thereby producing a medicine which is offered to a human body, by acquiring an action mechanism of the medicine based on the first optimal solution for the graph describing the RNA expression matrix,
wherein the plurality of first solutions are U×V solutions when U and V are respectively natural numbers, and
wherein the first maximum evaluation value estimation unit divides the U×V solutions into V blocks, acquires V division maximum values of evaluation values of U solutions for the respective blocks, and estimates the first maximum evaluation value using the V division maximum values assuming that the interval maximum values follow a generalized extreme value distribution.

13. The optimal solution determination device according to claim 12,
wherein the processor functions as:
a second solution extraction unit that uniformly extracts a plurality of solutions that are solutions in the solution space and are outside a range of a predetermined distance in the solution space from the first optimal solution, as a plurality of second solutions using the data structure obtained by contracting combinable patterns to form the data structure to be enumerated and indexed, or random generation;
a second evaluation value acquisition unit that acquires, based on an evaluation function, a plurality of second evaluation values respectively corresponding to the plurality of second solutions;
a second maximum evaluation value estimation unit that estimates a maximum evaluation value in a case where solutions of a number that exceeds the number of the plurality of second solutions are assumed, on the basis of the plurality of second evaluation values, and sets the estimated maximum evaluation value as a second maximum evaluation value; and
a second determination unit that acquires an evaluation value corresponding to the first optimal solution from the second evaluation value acquisition unit, and determines whether the acquired evaluation value corresponding to the first optimal solution exceeds the second maximum evaluation value,
wherein the plurality of second solutions are P×Q solutions when P and Q are respectively natural numbers, and
wherein the second maximum evaluation value estimation unit divides the P×Q solutions into Q blocks, acquires Q interval maximum values of evaluation values of P solutions for the respective blocks, and estimates the second maximum evaluation value using the Q interval maximum values assuming that the interval maximum values follow a generalized extreme value distribution.

* * * * *